United States Patent
Li et al.

(10) Patent No.: US 10,398,746 B2
(45) Date of Patent: Sep. 3, 2019

(54) EDIBLE ORAL STRIP OR WAFER DOSAGE FORM CONTAINING ION EXCHANGE RESIN FOR TASTE MASKING

(71) Applicant: LTS Lohmann Therapie-Systeme AG, Andernach (DE)

(72) Inventors: Michael Li, Martinsville, NJ (US); Markus Krumme, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 15/420,918

(22) Filed: Jan. 31, 2017

(65) Prior Publication Data

US 2017/0136078 A1 May 18, 2017

Related U.S. Application Data

(62) Division of application No. 14/123,490, filed as application No. PCT/EP2012/002291 on May 30, 2012, now Pat. No. 9,597,287.

(60) Provisional application No. 61/494,462, filed on Jun. 8, 2011.

(51) Int. Cl.

| | | |
|---|---|---|
| A61K 9/00 | (2006.01) | |
| A61K 36/47 | (2006.01) | |
| A61K 31/192 | (2006.01) | |
| A61K 47/18 | (2017.01) | |
| A61K 47/26 | (2006.01) | |
| A61K 47/38 | (2006.01) | |
| B29C 41/00 | (2006.01) | |
| A23L 27/00 | (2016.01) | |
| A61K 47/10 | (2017.01) | |
| A61K 47/32 | (2006.01) | |
| A61K 47/36 | (2006.01) | |
| A61K 47/46 | (2006.01) | |
| B29B 7/88 | (2006.01) | |
| B29B 13/00 | (2006.01) | |
| B29C 39/02 | (2006.01) | |
| B29C 39/36 | (2006.01) | |
| B29C 39/38 | (2006.01) | |
| B29C 69/00 | (2006.01) | |
| B29K 105/00 | (2006.01) | |
| B29L 7/00 | (2006.01) | |

(52) U.S. Cl.
CPC ............ *A61K 36/47* (2013.01); *A23L 27/88* (2016.08); *A61K 9/006* (2013.01); *A61K 31/192* (2013.01); *A61K 47/10* (2013.01); *A61K 47/186* (2013.01); *A61K 47/26* (2013.01); *A61K 47/32* (2013.01); *A61K 47/36* (2013.01); *A61K 47/38* (2013.01); *A61K 47/46* (2013.01); *B29B 7/88* (2013.01); *B29B 13/00* (2013.01); *B29C 39/02* (2013.01); *B29C 39/36* (2013.01); *B29C 39/38* (2013.01); *B29C 41/003* (2013.01); *B29C 69/001* (2013.01); *A23V 2002/00* (2013.01); *B29B 2013/005* (2013.01); *B29K 2105/0035* (2013.01); *B29L 2007/007* (2013.01)

(58) Field of Classification Search
None
See application file for complete search history.

(56) References Cited

U.S. PATENT DOCUMENTS

| | | | | |
|---|---|---|---|---|
| 5,200,192 | A | * 4/1993 | Wimmer | .............. A61K 9/0056 424/451 |
| 8,187,617 | B2 | * 5/2012 | Howard | .............. A61K 9/2054 424/400 |
| 8,282,954 | B2 | 10/2012 | Bogue et al. | |
| 8,613,285 | B2 | * 12/2013 | Fuisz | ...................... A24B 3/18 131/352 |
| 2002/0169212 | A1 | 11/2002 | Stroble et al. | |
| 2006/0204559 | A1 | 9/2006 | Bess et al. | |
| 2008/0003267 | A1 | 1/2008 | Spencer et al. | |
| 2009/0196907 | A1 | 8/2009 | Bunick et al. | |
| 2010/0285130 | A1 | 11/2010 | Sanghvi | |

FOREIGN PATENT DOCUMENTS

| | | |
|---|---|---|
| JP | 2009-530291 A | 8/2009 |
| JP | 2010-523581 A | 7/2010 |
| WO | WO 2001/39749 A2 | 6/2001 |
| WO | WO 2001/70194 A1 | 9/2001 |
| WO | WO 2006/047365 A1 | 5/2006 |
| WO | WO 2007/109057 A2 | 9/2007 |
| WO | WO 2009/048577 A1 | 4/2009 |

OTHER PUBLICATIONS

Dow Liquid Separations, Dowex Ion Exchange Resin, Jul. 2003.*
Amberlite IRP69 Product Information Sheet, Oct. 2011).*
Amberlite IRP69 Product Information Sheet, (Feb. 2006) (Year: 2006).*
Ali, Shaukat et al., BASF Polymers in Film Development Technology for Drug Delivery Applications, 32nd International Symposium on Controlled Release of Bioactive Materials, 2005, [online] http://www.pharma-ingredients.basf.com/documents/enp/poster/en/.

* cited by examiner

Primary Examiner — Robert A Wax
Assistant Examiner — Melissa S Mercier
(74) Attorney, Agent, or Firm — ProPat, L.L.C.

(57) ABSTRACT

An edible oral film strip dosage form containing an unpalatable basic active pharmaceutical ingredient and an ion exchange resin as a primary taste masking agent, along with an optional acidic agent and further optionally containing one or more secondary taste masking agents is provided. The edible oral film strip dosage matrix is formed from at least one water soluble or miscible polymer(s). The optional secondary taste masking ingredients include one or more of flavoring agent(s), sweetener(s), cooling sensation agent(s), and taste receptor blocker(s). Methods for preparing the inventive edible oral film strip dosage forms are disclosed, as well as their method of administration.

22 Claims, No Drawings

EDIBLE ORAL STRIP OR WAFER DOSAGE FORM CONTAINING ION EXCHANGE RESIN FOR TASTE MASKING

CROSS-REFERENCE TO RELATED APPLICATIONS

This application is a divisional of allowed U.S. patent application Ser. No. 14/123,490, filed Feb. 7, 2014, which claims priority to International Patent Application No. PCT/EP2012/002291, filed May, 30, 2012, which claims priority to U.S. Provisional Patent Application No. 61/494,462, filed Jun. 8, 2011. Each of U.S. patent application Ser. No. 14/123,490; International Patent Application No. PCT/EP2012/002291 and U.S. Provisional Patent Application No. 61/494,462 are hereby incorporated by reference herein in their entirety.

FIELD OF THE INVENTION

The present invention pertains to an edible oral film strip dosage forms containing one or more taste masking ingredients for the delivery and release of clinically active pharmaceutical ingredient(s) having poor palatability.

BACKGROUND OF THE INVENTION

Non-steroidal anti-inflammatory drugs (NSAID) are drugs with analgesic and antipyretic effects. NSAIDs can be classified based on their chemical structure, including propionic acid derivatives, acetic acid derivatives and enolic acid derivatives, inter alia. Propionic acid derivates include ibuprofen, naproxen and ketoprofen. Ketoprofen, one of the most potent NSAIDs, is well known for treating symptoms associated with chronic arthritis, osteoarthritis, acute tendonitis, bursitis, headaches, migraines, chronic neuropathic pains, shingles, premenstrual symptoms, sports injuries and like.

Traditionally, ketoprofen has been marketed in various tablet dosage forms. However, tablets may not be suitable for juvenile, certain general public and geriatric populations who have difficulty in swallowing. The requirement of additional water and oral liquids to facilitate swallowing further hampers the successful administration of tablet dosage forms in the aforementioned patient populations.

Edible oral strip/wafer thin film (hereinafter "oral thin film") dosage forms for delivering active pharmaceutical agents are one avenue by which to facilitate self-administration of medications and enhance patient compliance and adherence. Edible oral film strip dosage forms generally incorporate an active ingredient into a thin film for subsequently delivery, which is conventionally delivery primarily via the oral mucosa. The edible oral film strip dosage forms more specifically incorporate clinically active pharmaceutical ingredients which can be easily dispersed and disintegrated in the saliva of the oral cavity without water or additional oral liquids to allow for easy swallowing. To date, only a very small number of edible oral film strip dosages are commercially available that incorporate therapeutically active pharmaceutical ingredients, however.

Unfortunately, ketoprofen has an unpleasant bitter taste with a burning sensation, limiting its incorporation into edible oral film strips. Ketoprofen also irritates the throat mucosal membrane during swallowing. However, in view of recently renewed interest for clinically proven and safer pain medications due to Cox 2 inhibitor's unwanted side effects, the successful development of an edible oral strip/wafer thin film dosage form containing Ketoprofen is of significant commercial interest.

Heretofore, those skilled in the at have considered the development of an edible oral film strip dosage form containing ketoprofen to be an exceptionally intricate formulation challenge. Particularly, it has been heretofore understood by those skilled in the art that the complete masking of the bitter taste and burning sensation of ketoprofen would not be possible.

United States Patent Application Publication No. 2002/0169212 discloses an animal health solution formulation of ketoprofen in water. The solution medication is prepared by solubilizing ketoprofen with a weak base in water. A weak base and Ketoprofen in a ratio of 10 to 1 were utilized to solubilize the ketoprofen in water. Additional flavoring and sweetening agents were added to the aqueous ketoprofen solution to increase the palatability of the solution. This publication, however, does not disclose a dosage form containing a taste masked Ketoprofen active.

International Patent Application No. WO 2007/109057 A2, whose United States equivalent is United States Patent Application Publication No. 2007/0292515, discloses a thin film dosage form using Ketoprofen as the active ingredient that has been neutralized with an edible alkaline agent(s) to mask the unpleasant taste of the Ketoprofen. This publication does not utilize alternate and multiple synergistic taste masking strategies to further and completely mask the unpleasant taste of Ketoprofen, however. In regard, in early 2005 the instant inventors performed tests which determined that the neutralization of Ketoprofen using ordinary laboratory edible alkaline agents, such as those used in WO 2007/109057, could not block the entirety of the unpleasant tastes of Ketoprofen successfully.

Therefore there remains a strong need in the art to develop a more robust edible oral film strip dosage forms that can deliver unpalatable active pharmaceutical ingredient(s), such as unpalatable NSAIDs, in the oral cavity. There particularly remains a strong need in the art to develop edible oral film strip dosage forms that eliminate the adverse bitter taste, burning sensation and throat irritation of ketoprofen.

SUMMARY OF ADVANTAGEOUS EMBODIMENTS OF THE INVENTION

Altogether unexpectedly, the present invention provides an edible oral strip/wafer thin film dosage form that minimizes or eliminates altogether the unpleasant taste and burning sensation generally associated with acidic active pharmaceutical ingredients, particularly acid-based NSAIDS such as Ketoprofen. The present invention particularly comprises saliva dispersible and disintegrable thin film(s) containing an effective amount of an unpalatable acidic active pharmaceutical ingredient, such as Ketoprofen, along with a primary and optional secondary taste masking agents. The primary taste masking agent is an ion exchange resin, particularly an anion exchange resin. The secondary taste masking agent is selected from one or more of taste receptor blocking agents, cooling sensation agents, sweeteners and flavoring agents.

The present invention thus pertains to an edible oral strip form containing ion exchange resin(s) as a primary taste masking agent and optionally further including secondary taste masking agents for the delivery and release of an effective amount of an unpalatable clinically active pharmaceutical ingredient, for example, Ketoprofen, from a film forming polymer matrices. The inventive edible oral strip delivers and releases the clinically active ingredient(s) into the oral cavity with subsequent absorption via the oral mucosa.

In particularly advantageous embodiments, the inventive edible oral film strip dosage forms further include an edible pH adjustment agent(s) to facilitate ionic binding of the active pharmaceutical ingredient to the ion exchange resin.

Further inventive aspects include methods by which to form the inventive oral film strips, as well as their subsequent administration.

DETAILED DESCRIPTION OF ADVANTAGEOUS EMBODIMENTS OF THE INVENTION

The inventive edible oral film strips are formed from saliva dispersible and disintegrable thin film(s) or sheets that further contain an unpalatable acidic active pharmaceutical, cosmetic or food-related ingredient and at least one anion exchange resin as a primary taste masking agent, along with optional edible pH adjustment agent(s), secondary taste masking agent(s) and emulsifier(s). The oral film strip disintegrates when applied to the oral cavity to release the taste masked active ingredient, which is then swallowed to be absorbed. The inventive oral film strip particularly disperses easily in the saliva of oral cavity and then releases a clinically effective amount of the taste-masked active agent to be absorbed by the patient.

The saliva dispersible and disintegrable thin films used to form the inventive oral film strip matrices may be any known monographed film-forming material known in the art for use in flat-shaped or wafer-shaped administration forms for application to the oral region or on the mucous membranes of the mouth. The inventive oral film strips generally comprise at least one water-soluble and/or water-dispersible film-forming polymer, particularly at least one saliva-soluble and/or saliva-dispersible film-forming polymer, that is capable of forming a suitably strong film upon casting in a pharmacologically acceptable solvent.

Exemplary water-soluble or water-miscible polymers suitable for use as the film-forming or matrix-forming material within the inventive oral film strips include, but are not limited to, one of more of cellulose, cellulose derivatives, synthetic or natural gums, such as, xanthan gum, tragacanth gum, guar gum, acacia gum, arabic gum. Locust bean gum,
methacrylic acid polymers, methacrylic acid copolymers, acrylic acid polymers, acrylic acid copolymers, polyacrylamides, polyalkylene oxides, polyalkylene glycols, carrageenan, pullunan, locust bean gums, bean starches, polyvinyl pyrrolidone, polyvinyl alcohol, alginic acid, salts of alginic acid, carboxyvinyl polymers, pectin, pectin derivatives, xanthan gum, xanthan gum derivatives, pea starch, starch starch derivatives, carrageenan, alginic acid, salts of alginic acid and mixtures thereof. In particularly advantageous embodiments, a mixture of two of more more film-forming or matrix-forming materials is incorporated into the inventive oral film strips.

Suitable gums for producing the inventive oral film strips include xanthan gum, tragacanth gum, guar gum, acacia gum, arabic gum, locust bean gum, and mixtures thereof.

Exemplary cellulose derivatives suitable for use in forming the inventive oral film strips include methyl cellulose, ethyl cellulose, hydroxyethyl cellulose, hydroxypropyl methyl cellulose, carboxymethyl cellulose, sodium carboxymethyl cellulose, and mixtures thereof. In particularly advantageous embodiments, the inventive oral film strips are formed from a mixture of sodium carboxymethylcellulose or hydroxypropylmethyl cellulose and/or hydroxypropylcellulose. Sodium carboxymethylcellulose, commonly referred to as cellulose gum, is commercially available from any of a number of suppliers, including as AQUALON® CMC-7LF sodium carboxymethyl cellulose ("CMC") from Ashland Inc., of Covington, Ky. Hydroxypropylmethyl cellulose ("HPMC"), also referred to as hypromellose, is commercially available from a number of suppliers, including as METHOCEL® from Dow Chemical Company, Midland, Mich., BENECEL® from Ashland, Inc. of Covington, Ky. and PHARMACOAT® from Shin-Etsu Chemical Col, Ltd. of Tokyo, Japan and METOLOSE®, also from Shin Etsu Chemical Co. Ltd of Tokyo. Hydroxypropylcellulose ("HPC") is commercially available as KLUCEL® from Hercules Incorporated Wilmington, Del.

Advantageously, the inventive oral film strips incorporate a film-forming mixture containing both lower and higher viscosity cellulose derivatives. The inventive oral film strips may incorporate a mixture of lower and higher viscosity HPMCs, for example. An exemplary range for the lower viscosity cellulose derivatives is from about 1.5 to 25 mPas, such as about 2 to 20 mPas, particularly about 3 mPas. An exemplary range for the higher viscosity cellulose derivative is from about greater than 25 to 100 mPas, such as from about 40 to 80 mPas, particularly about 50 mPas. HPMC having a viscosity of 3 mPas is commercially available as PHARMACOAT® 603 and HPMC having a viscosity of 50 is commercially available as METOLOSE® 60 SH50. The lower viscosity cellulose derivative is generally present within the film-forming mixture in a greater amount than the higher viscosity cellulose derivative. The lower viscosity cellulose derivative may be present within the film-forming mixture in any effective weight ratio in comparison to the higher viscosity cellulose derivative, such as a weight ratio ranging from about 1.5:1 to 6:1, particularly about 2.0:1 to 4:1, such as about 3:1 (lower viscosity cellulose derivative: higher viscosity cellulose derivative).

In particularly expedient embodiments, a mixture of sodium carboxymethylcellulose and hydroxypropylmethyl cellulose is used as the film-forming material or matrix, as this mixture has been determined to have both excellent film forming capabilities, oral film strip handling characteristics, beneficial mouth-feel, as well as a fast dissolution time. The particular ratio of sodium carboxymethylcellulose to hydroxypropylmethyl cellulose is chosen to yield the desirable dissolution times and mouth-feel for a reasonably thin film and to further impart acceptable product handling characteristics. Although not wishing to be bound by theory, Applicants hypothesize that carboxymethyl cellulose imparts ease of dissolution in the mouth and robust mouth-feel, while hydroxypropylmethyl cellulose imparts improved mechanical strength, particularly improved tear strength.

The film-forming material or matrix is generally present within the inventive oral film strips in amounts ranging from about 5 weight percent (wt %) to 75 wt %, particularly from about 15 to 50 wt %, based on the weight of the dry oral film strip. Exemplary amounts of sodium carboxymethylcellulose ranges from about 7 to 40 wt %, based on the weight of the dry oral film strip. Exemplary amounts of hydroxyl propyl methyl cellulose range from 3.5 to 14 wt %, based on the weight of the dry oral film strip. Exemplary amounts of hydroxypropyl cellulose ranges from about 10 to 40 wt %, based on the weight of the dry oral film strip. Exemplary amounts of pectin range from about 4 to 25 wt %, based on the weight of the dry oral film strip.

Suitable active ingredients for incorporation within the inventive oral film strips include any unpalatable acidic active pharmaceutical ingredient, particularly any unpalatable NSAID. Exemplary NSAIDs include salicylates, such as aspirin, propionine acid derivatives, acetic acid derivatives, enolic acid derivatives and fenamic acid derivatives. Exemplary propionic acid NSAIDS include ketoprofen, ibuprofen, naproxen, fenoprofen, flurbiprofen, oxaprozin and loxoprofen.

In particularly advantageous embodiments, the active ingredient is ketoprofen, also known as (RS)-2-(3-benzoylphenyl) propanoic acid, having the chemical formula $C_{16}H_{14}O_3$. Ketoprofen is a white, crystalline powder, that is slightly soluble in water, soluble in ether, alcohol, acetone, chloroform, DMF and ethyl acetate. The active ingredient may be present in any amount effective to impart sufficient analgesic and antipyretic effects, particularly any amount effective to reduce or alleviate pain. Exemplary clinically effective amounts of active ingredient, such as ketoprofen, that may be included in the inventive oral film strips generally ranges from about 3 mg to about 75 mg per oral film strip unit (i.e. per dosage), particularly from about 4 to 50 mg per oral film strip unit, specifically from about 6 to 25 mg per oral film strip unit based upon the weight of the dry oral film strip. Applicants further respectfully submit that conventional tablets contain significantly greater amounts of active ingredient than are required within the inventive oral film strips.

Exemplary weight percentages of active ingredient, particularly of ketoprofen, that may be included within the inventive oral film strips range from about 10 to 50 wt %, such as from about 20 to 36 wt %, based upon the dry oral film strip.

Altogether unexpectedly, Applicants have found that the addition of at least a primary taste masking agent in the form of one or more anionic ion exchange resins within the inventive oral film strips greatly reduces or altogether eliminates the unpleasant tastes and burning sensation associated with acidic active ingredients, specifically with ketoprofen. In particularly expedient embodiments, a synergistic blend of taste masking agents is incorporated into the inventive oral film strips, specifically a blend including one or more anionic ion exchange resins as a primary taste masking agent, along with one or more secondary taste masking agents selected from sweetener(s), flavouring agent(s), cooling sensation agent(s), and taste receptor blocker(s).

As used herein, the term "taste masking" means substantially or completely reducing or eliminating the bitter taste, burning sensation and/or throat irritation heretofore normally associated with many acidic active ingredients, particularly ketoprofen.

Exemplary anionic ion exchange resins ("anion exchange resins") for incorporation as primary taste masking agents in the inventive oral film strips include any known pharmacologically acceptable and compendium approved anion exchange resin, particularly any known insoluble, strongly basic anion exchange resin. In particularly advantageous embodiments, cholestyramine resin USP, a known anion exchange resin, is incorporated into the inventive oral film strips as the primary taste masking agent. Cholestyramine resin is commercially available as DUOLITE® resin from Dow Chemical Corporation of Midland, Mich.

Surprisingly, Applicants found that both the taste and chemical stability of the inventive oral film strips are improved dramatically upon binding the active ingredient to an anionic ion exchange resin. The anion exchange resin is incorporated in amounts allowing for the maximum binding of the active ingredient at the therapeutic drug concentration while retaining an acceptable film strength for the oral film strip, thereby providing maximum taste masking capability without detriment to the resulting oral film strip physical properties.

The anionic ion exchange resin is more particularly included in a sufficient amount to bind the active pharmaceutical ingredient, e.g. ketoprofen, thereby diminishing its bitter taste, burning sensation and throat irritation without significantly detrimentally impacting the physical properties of the resulting oral film strip. Exemplary effective amounts of anion exchange resin included in the inventive oral film strips range from about 12 to 50 wt %, such as from about 20 to 40 wt %, based on the weight of the dry oral film strip.

The active ingredient and anion exchange resin are generally present in a roughly equal weight ratio, such as a weight ratio ranging from about 0.9:1 (active ingredient:anion exchange resin) to 1.5 to 1 (active ingredient:anion exchange resin). In particularly expedient embodiments, the active ingredient is present in a slight excess in comparison to the anion exchange resin, such as a ratio of about 1.02:1 to 1.1:1 (active ingredient:anion exchange resin).

Applicants have further determined that the binding of the acidic active ingredient to the anion exchange resin may be improved by increasing the pH of the active ingredient solution using an alkaline or basic agent. Many acidic active ingredient solutions in water, acetone or a hydroalcoholic solvent, such as a ketoprofen solution based on the foregoing solvents, generally have a pH of about 4.0. Applicants have found that the pH range of the acidic active pharmaceutical ingredient should be adjusted to an optimum pH range of from about 5.0 to 10.0, such as from about 6.0 to 8.0, to ensure maximum binding of the active pharmaceutical ingredient to the ion exchange resin.

Any edible or pharmacologically acceptable pH increasing alkaline or basic agent may be utilized to increase the pH of the acidic active ingredient to the optimum range. Exemplary pH increasing agents include hydroxides, edible bicarbonates, edible, carbonates, basic amino acids, buffers and mixtures thereof. Suitable hydroxides for increasing the pH of the acidic active ingredient include sodium hydroxide, calcium hydroxide, magnesium hydroxide, potassium hydroxide and mixtures thereof. Suitable edible carbonates include alkali metal carbonates, such as calcium carbonate, sodium carbonate and potassium carbonate. Exemplary edible bicarbonates include alkali metal bicarbonates, such as sodium bicarbonate and potassium bicarbonate. Exemplary basic amino acids include lysine and arginine. Exemplary buffers include sodium phosphate buffers, potassium phosphate buffers; sodium citrate buffers and potassium citrate buffers.

Exemplary amounts of alkaline or basic agents required to sufficiently increase the pH of the inventive oral film strips range from about 1.5 to 10 wt %, such as from about 3.5 to 6.5 wt %, based upon the weight of the dry oral film strip.

Although the taste masking of the active ingredient is achieved primarily by binding of the active ingredient with an effective amount of anionic exchange resin, the inventive oral film strips may additionally beneficially include one or more secondary taste masking agents to further block any residual unpleasant taste associated with the active pharmaceutical ingredient. In especially advantageous embodiments, the secondary taste masking agents completely block any residual unpleasant taste associated with the active pharmaceutical ingredient, i.e. the inventive oral film strips have no bitter taste, burning sensation and/or throat irritation during ingestion.

Exemplary secondary taste masking ingredients include one or more of sweetener(s), flavouring agents, cooling sensation agent(s), and taste receptor blocker(s). In especially expedient embodiments, multiple components are contained within the secondary taste masking composition or blend.

Exemplary sweeteners include dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin, dextrates and mixtures thereof. Particularly advantageous sweeteners for incorporation within the inventive oral film strips include isomalt, sucralose, aspartame, saccharine and acesulfame sweetener, and mixtures thereof. In particularly expedient embodiments, the inventive oral film strips include more than one sweetener, such as a sweetener composition containing two sweeteners. In especially expedient aspects of such embodiments, isomalt is used as an adjunct sweetener in addition u, a primary sweetener, particularly a primary sweetener selected from one or more of sucralose, aspartame, saccharine and acesulfame. Isomalt is commercially available as ISOMALTIDEX® from Cargill Incorporated, Minnetonka, Minn. In especially expedient embodiments, isomalt is used as an adjunct sweetener in addition to a primary sweetener selected from one or more of sucralose, aspartame, saccharine and acesulfame. In such embodiments, the isomalt is generally present as the adjunct sweetener in amounts franging from about 1.5 to 7 wt %, such as from 3.5 to 4.5 wt %, based upon the weight of the dry oral film strip.

The overall sweetener composition or primary sweetener portion may be included in any effective amount, such as from about 0.25 to 3 weight %, such as from about 0.5 to 1.6 weight percent, based upon the weight of the dry oral film strip.

Exemplary flavouring agents include various essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, tutti fruitti, apple, coffee, plum, watermelon, nuts, green tea, grapefruit, banana, butter, chamomile, masking flavour, and mixtures thereof. In especially beneficial embodiments the inventive oral film strips incorporate one or more flavouring agents selected from lime, tutti frutti, cherry, wintergreen, spearmint, peppermint, and orange. Suitable pharmaceutical grade flavouring agents may by acquired from any of a number of suppliers. In addition to their use as flavorants, several of the foregoing flavouring agents may serve as cooling agents, as well.

The flavouring agents may be included in any effective amount, such as from about 0.3 to about 4.5 weight %, such as from about 0.6 to 3.5 wt %, based upon the weight of the dry oral film strip.

A masking flavour may also be incorporated within the inventive oral film strips, particularly in combination with further flavouring agents. Masking flavours are commercially available from a number of suppliers, including Firmenich of Geneva, Switzerland. The masking flavouring may be included in any effective amount, such as from about 0.34 to about 2.5 wt %, such as from about 0.65 to 1.70 wt %, based upon the weight of the dry oral film strip.

One or more cooling sensation agents may also advantageously be included as a secondary taste masking agent within the inventive oral film strips to diminish or altogether eliminate any burning sensation, particularly any residual burning sensation, associated with the acidic active ingredient subsequent to the addition of the primary taste masking agent. Exemplary cooling sensation agents include essential oils or extracts of menthol, wintergreen, peppermint, sweet mint, spearmint, and mixtures thereof.

The cooling sensation agent may be included in any effective amount, such as from about 0.7 to about 3.0 weight %, such as from about 1.3 to 2.5 wt %, based upon the weight of the dry oral film strip.

One or more taste receptor blockers may also advantageously be included as a secondary taste masking agent within the inventive oral film strips. Exemplary taste receptor blockers include any monographed taste receptor blocker. In expedient embodiments, the inventive oral film strips include PEG-40 hydrogenated castor oil as taste receptor blocker. PEG-40 Hydrogenated Castor Oil is commercially available as CREMOPHOR® from BASF SE of Ludwigshafen, Germany.

The taste receptor blockers may be included in any effective amount, such as from about 0.17 to about 6.5 weight %, and particularly from about 0.30 to 4.50 wt %, based upon the weight of the dry oral film strip.

The inventive oral film strips can additionally beneficially include at least one emulsifier to stabilize the flavours within the aqueous phase during oral film strip processing. Any well-known water-soluble monographed emulsifier is suitable for use in the inventive oral film strips. The examples of suitable emulsifying agents include, but are not limited to, castor oil derivatives, cetyl and palmityl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, polyethylene sorbitan fatty acid esters and mixtures thereof. Exemplary emulsifiers include polysorbate 80, also known as polyoxyethylene-sorbitan-20-monooleate, commercially available from a wide variety of of suppliers.

The emulsifier may be included within the inventive oral film strips in any amount effective to stabilize the flavouring agents within the aqueous phase during oral film strip processing. The emulsifier may generally be present within the inventive oral film strips in amounts ranging from about 0.25 to 2.25 wt %, such as from 0.50 to 1.50 wt, based on the weight of the dry oral film strip.

Additional ancillary components suitable for incorporation within the inventive oral film strips include, but are not limited to one or more of the following pharmaceutically-acceptable excipients:bioadhesives for mucosal binding (also referred to as mucoadhesives), buffering agents for additional pH control, coloring agents, stabilizing agents, antioxidants, fillers, permeation enhancers, plasticizers and microbial preservatives. Such ancillary components are included within the inventive oral film strips in amounts considered conventional by one skilled in the art for the given component.

Mucoadhesive(s) adhere to the oral mucosal membranes, such as the surfaces of cheek, palate or tongue for local absorption and prolonged action, as known in the art. Exemplary mucoadhesives include edible silicone and polyacrylic acids, particularly polymers of acrylic acid cross-linked with polyalkenyl ethers or divinyl glycol such as the family of CARBOPOL® polymers, commercially available from Lubrizol Corporation of Wickliffe, Ohio.

The examples of suitable colorants include approved edible pigments, dyes, natural food colors, and synthetic colorants such as FD&C coloring agents and mixtures thereof.

The examples of suitable stabilizers and/or antioxidants include chelating agents, such as ethylenediaminetetraacetic acid ("EDTA"), ethylene glycol tetraacetic acid ("EGTA"), sodium bisulfite, sodium metabisulfite, ascorbic acid, ascorbyl palmitate and mixtures thereof.

Exemplary fillers include any water soluble inert filler. Suitable water soluble inert fillers for incorporation in the inventive oral film strips include mannitol, xylitol, glucose, fructose, sucrose, sucralose, lactose, trehalose, maltodextrin, dextran, dextrin, modified starches, dextrose, sorbitol, dextrates and mixtures thereof.

The edible oral thin film may also contain natural or synthetic permeation enhancers suitable for active pharmaceutical ingredient(s) via the mouth mucosal and/or GI tract surface. As well understood in the art, a "permeation enhancer" is a natural or synthetic compound which facilitates the absorption of an active agent through a mucosal surface. Exemplary permeation enhancers include anionic surfactants, such as sodium lauryl sulfate and sodium laurate; cationic surfactants, such as cetylpyridium chloride; non-ionic surfactants, such as poloxamer, Brij, Span, Myrj, and Tween; bile salts; sodium glycodeoxycholate; sodium glycocholate, sodium taurodeoxycholate, sodium taurocholate, Azone®; fatty acids, such as oleic and caprylic acid; cyclodextrins, such as α-, β-, γ-cyclodextrin, methylated β-cyclodextrins; chelators, such as EDTA, sodium citrate and poly acrylates; polymers, such as chitosan, trimethyl chitosan and cationic amino acids, such as poly-L-arginine and L-lysine. Brij is the tradename for a family of nonionic polyoxyethylene commercially available from a number of suppliers. Span is the tradename for a family of sorbitan surfactants, such as sorbitan trioleate (Span 85) and sorbitan tristearate (Span 65) and the like, commercially available from a number of suppliers. Myrj is a tradename for a family of polyethoxylated fatty acid commercially available from a number of suppliers, such as polyoxyethylene monostearate (Myrj 49) and the like. Tween is the tradename for a family of polyoxyethylene sorbitan or polysorbate surfactants, such as polyoxyethylene sorbitan trioleate (Tween 85) and polysorbate 80 (Tween 80) commercially available from a number of suppliers. Azone is a tradename for 1-Dodecylhexahydro-2h-Azepin-2-One Suitable plasticizers include, but not limited to, alkylene glycols, polyalkylene glycols, glycerol, triacetin, deacetylated monoglyceride, polyethylene glycols, diethyl salate, triethyl citrate, and mixtures thereof.

The edible oral film strip oral film strip form may also contain microbial preservatives, such as butylated hydroxyanisol, butylated hydroxytoluene, parabens, parabens derivatives, sorbic acids and derivatives, benzoic acid and derivatives, propionic acid and derivatives, acetic acid and derivatives and mixtures thereof.

The inventive oral film strips may be in the form of either a single or multiple layered film. For multi-layered embodiments, each or the individual layers may contain either identical or different excipients in either the same or differing amounts. Various film layers may be formulated to exhibit differing dissolution times or contain various active ingredient loadings, for example. The inventive oral film strips are prepared in thicknesses conventional with wafer or thin film-based oral film strips, such as thicknesses ranging from 50 to 120 microns, particularly about 60 to 115 microns.

Suitable solvents suitable for use in forming the inventive oral film strips include one or more of purified water, acetone, ethanol or other pharmacologically acceptable alcohol that is 4 carbons or less in length. The pharmacologically acceptable solvents may be used in any combination and any solvent ratio. In particularly advantageous embodiments, the inventive oral film strips are formed using a solvent composition that includes acetone, ethanol or other alcohol as co-solvent, along with water as the primary solvent. The co-solvent may be present within the solvent composition in amounts generally ranging from about 5 to 75%, such as an amount ranging from about 25 up to 50%, based on the total weight of the solvent composition.

The solvents are used in amounts effective to dissolve and/or suspend the entirely of the ingredients into a liquid mass prior to oral film strip formation, particularly oral film strip casting, coating or extrusion. The resulting liquid mass has a moderately elevated viscosity, as is conventional for film-forming blends used to form edible oral film strip oral film strips. The solvent may be present in amounts of up to 95% within the liquid mass, such as an amount ranging from about 60 to 90%, based on the weight of the casting/coating/extrusion composition. The solvent is then removed after casting, coating or extruding the wet film in a subsequent drying step during oral film strip production.

The present invention further provides method for preparing an edible oral film strip oral film strip form. The inventive method generally includes combining a clinically effective oral film strip of acidic active pharmaceutical ingredient, e.g. ketoprofen, that has optionally had its pH adjusted to provide optimum binding characteristics with an anion exchange resin. Exemplary inventive methods more particularly include admixing the active pharmaceutical ingredient, e.g. ketoprofen, in a solvent selected from water, acetone and/or alcohol, optionally adjusting the pH of the resulting active ingredient solution, and subsequently introducing an effective amount of anionic ion exchanger(s) into the active ingredient solution. The optionally pH adjusted active ingredient solution containing the anion exchange resin may then be admixed with one or more water-soluble or water-miscible polymers to provide a film-forming solution having adequate physical stability. Optional excipients, including cooling agents, emulsifiers, flavouring agents, sweeteners, taste receptor blockers and ancillary excipients, may then be added to complete the film-forming composition. Prior to film formation, the viscous homogenous mixture can be sonicated, aspirated and/or vacuumed to remove air entrapped within the film forming composition. The optionally deaerated film forming composition is subsequently formed into a thin film having a defined wet thickness using processes well known in the art, such as by casting, coating or extrusion. More particularly, the inventive film forming composition may be cast, coated or extruded onto a suitable casting substrate, thereby forming a wet film having a defined wet thickness. This wet film may then be dried, such as with a uniform laminar flow heating oven or other suitable dryers, using conventional process equipment and conditions well known to those skilled in the art. The dried film may then be removed from the coating substrate and subsequently be cut into various geometric shapes and sizes using a suitable cutting method, such as, die cutting, punching, knife, or rotary cutting machine.

In particularly advantageous embodiments, the inventive methods involve dispersing an effective amount of ketoprofen in water, acetone or hydroalcoholic cosolvent, generally resulting in a ketoprofen solution pH of about 4.0. The pH of the ketoprofen solution is subsequently adjusted to pH from 5.0 to 10.0 to provide for optimum binding with a strongly basic anionic exchange resin; and a strongly basic anionic exchange resin, such as cholestyramine, is then admixed into the pH adjusted ketoprofen solution. The anionic exchange resin/ketoprofen mixture is then uniformly admixed with water soluble or miscible polymers which will form the film matrices and enhance the chemical and physical stability of the resulting film. Excipients such as menthol, flavours, isomalt and other sweetener ingredients can then be utilized to give the optimum cooling and sweet sensation on the tongue. PEG-40 hydrogenated castor oil, an additional excipient, can also be added as a taste receptor blocker, to control any residual bitterness or burning sensation associated with the active ingredient or other excipients. The film forming composition containing ketoprofen, anion exchange resin, water soluble polymer and optional excipient composition is then subjected to sufficient mixing to produce a smooth, viscous mixture. This viscous mixture may be deaerated subsequent to mixing and then cast onto a casting substrate using conventional coating equipment. The cast film is then dried, removed from the casting substrate and cut into strips and wafers of various geometric shapes. Exemplary shapes for the inventive oral film strips include with any geometric shape, such as round, oval, square and rectangular and any other irregular geometric shapes.

Methods of administering the inventive oral film strips are also provided herein. The inventive methods of administering generally comprise applying or disposing a clinically effective dose of the inventive taste-masked active ingredient to the oral cavity of a patient or individual and allowing it to dissolve or disintegrate, advantageously without additional water or oral liquids other than saliva, to be subsequently absorbed in the GI tract of a patient or individual. Advantageously, the inventive oral film strips have a dissolution time of less than 15 minutes, such as dissolution time of less than 5 minutes, and most preferably a dissolution time of less than 1 minute, based upon a 10 $cm^2$ oral film strip submerged in physiological fluids or an artificial simulation of such fluids.

In advantageous embodiments, the inventive methods of administration relates to the use of the inventive oral film strip to administer a clinically effective dose of taste-masked ketoprofen or other NSAID to the oral cavity of an individual for its subsequent absorption in the GI tract to alleviate symptoms associated with clinical disease states or conditions. Applicants respectfully submit that the advantageous binding of the active ingredient to the anionic exchange resin, particularly via pH adjustment, allows release of the active ingredient, e.g. ketoprofen, within the stomach where it is taken up quite rapidly. This unique formulation allows for very rapid pain relief. For example oral film strips incorporating ketoprofen can potentially relieve headache symptoms within 5 to 10 minutes.

The inventive taste-masked oral film strips may be used to treat symptoms associated with any of a number of disease states or conditions, including chronic arthritis, osteoarthritis, acute tendonitis, bursitis, headaches, migraines, chronic neuropathic pains, shingles, premenstrual symptoms, sports injuries and other chronic pains and like conditions. The inventive oral film strips are designed to quickly disintegrate and disperse or dissolve in the oral cavity for easy swallowing and subsequent release of the active pharmaceutical ingredient for absorption in the GI tract. The inventive oral film strips may be self-administered as needed by an individual to alleviate symptoms associated with one or more of the foregoing disease states or conditions. Alternatively, the oral film strip may be applied, particularly by a medical professional, to the oral cavity by means of mucoadhesive(s) to adhere to the mucosal membranes, such as the surfaces of the cheek, palate or tongue for local absorption and prolonged pain relieving action.

The inventive oral film strips incorporating effective amounts of ketoprofen generally take effect beginning after about 5 minutes, with the effect lasting up to 3 hours. Consequently, the inventive oral film strips are very robust, with fast onset, low dosage amount in comparison to conventional tablets, easily transported, and easily administered with long shelf life.

While the taste masked acidic active ingredient has been described herein within respect to disintegrating oral wafers or thin films, the taste masked acidic active ingredient may be incorporated into a wide variety of pharmacologically acceptable solid dosage forms. For example, the taste masked acidic active ingredient may be incorporated into an orally disintegrating tablet that rapidly disintegrates in the oral cavity and releases the active ingredient to be swallowed.

In that regard, the ion exchange resin technology described in this invention can be applied to any known dosage forms, including films, tablets, oral liquids, creams, etc. Particularly, any dosage form may be formed by forming a mixture of active ingredient(s), water soluble polymer(s), ionic exchange resin(s), optional pH adjustment agent, secondary taste masking agents and auxiliary excipients in the same ratios described in this invention. The resulting mixtures can be either in solid or liquid form, provided that the liquid form can be lyophilized to rid of the solvents if the dosage form is intended to be compressed into tablets.

As noted above, Applicants have performed testing and determined that the heretofore known edible oral film strip dosage forms containing Ketoprofen tasted bitter and further caused considerable throat irritation. Altogether unexpectedly, Applicants found that the binding of Ketoprofen to ion exchange resin, especially via pH adjustment, allowed for more successful taste masking of Ketoprofen.

Applicants further note that the inventive taste masked edible oral films are useful to deliver various active pharmaceutical ingredients with adverse taste. The oral film strip form may be administered without water and edible liquids to allow for easy patient adherence and compliance especially for the young, certain general and geriatric patients who have difficulty for swallowing.

Applicant additionally note that, although the invention is primarily directed to active ingredients attracted to anionic ion exchange resins, i.e. active pharmaceutical ingredients having a negative charge, the present invention is not limited to such active ingredient. Particularly, it is within the scope of the invention that clinically active pharmaceutical ingredients with positive charges could be bound to cationic ion exchange resins. Particularly, oral film strips may be formed by forming a mixture of active ingredient(s) with a positive charge (i.e. a basic active ingredient), film-forming polymer(s), cationic ion exchange resin(s), secondary taste masking agents and auxiliary excipients in the same ratios described in this invention, with the exception that an optional edible acidic agent would be used in lieu of the optional alkaline or basic agent, and the pH would thus be adjusted to become more acidic.

EXAMPLES

The non-limiting examples which follow are provided solely to illustrate particularly advantageous embodiments of the invention and expedient associated methods for forming the same.

The inventive oral film strips below were formed at ambient temperatures, i.e. a temperature of approximately 23° C., and atmospheric pressure, unless indicated to the contrary or otherwise obvious from the context.

Example 1

Disintegrable oral films containing a taste masked ketoprofen were produced from the following ingredients:

| Ingredient | Quantity (g) |
|---|---|
| Ketoprofen | 6.54 |
| Sodium Hydroxide | 1.54 |
| Anion exchange resin | 6.42 |
| LV HPMC | 6.79 |
| HV HPMC | 2.29 |
| Masking Flavor | 0.20 |
| Menthol | 0.40 |
| PEG-40 Hydrogenated Castor Oil | 0.16 |
| Sucralose | 0.16 |
| Lysine Hydrochloride | 2.34 |
| Ethanol | 30.25 |
| Purified Water | 43.48 |
| Total | 100.57 |

A solvent mixture containing about 43.48 g water and 30.25 g ethanol was initially charged into a vessel. About 6.54 g of ketoprofen was then added to the solvent mixture and mixed until, sonicated for 5 minutes, and mixed at 500 rpm. The pH of the ketoprofen/solvent solution was then adjusted using 1 N NaOH until the pH was above 5.5, resulting in an overall add of 1.54 g NaOH. About 6.42 g of DUOLITE® 1083 cholestyramine ion exchange resin was then slowly added to the pH adjusted ketoprofen solution under mixing. About 2.34 g of lysine hydrochloride was then added to further control the pH for maximum drug binding of the Ketoprofen to the ion exchange resin. About 0.20 g of masking flavour, about 0.4 g menthol, about 0.16 g CREMOPHOR® ELP PEG-40 hydrogenated castor oil and 0.16 g sacralise were then added and mixed at 500 rpm. About 6.79 g of lower viscosity PARMACOAT® 603 hydroxypropyl methyl cellulose ("LV HPMC") and about 2.29 g of higher viscosity METOLOSE® 60SH50 hydroxypropyl methylcellulose ("HV HPMC"), both from Shin Etsu Chemical Co. Ltd of Tokyo, Japan were added to the ketoprofen/solvent/taste masking agent composition and the resulting coating solution was sonicated for about 5 minutes. The sonicated coating solution was then formed into monolayered wafers using a conventional coating technique. The average weight of the resulting wafer was 77.66 mg (sd=4.25 mg) and the thickness was 115 μm (sd=8.2 μm). Wafers formed in accordance with Example 1 had no bitterness and/or throat irritation.

Example 2

Disintegrable oral films containing a taste masked ketoprofen were produced from the following ingredients:

| Component | Quantity (g) |
|---|---|
| Ketoprofen | 6.57 |
| Sodium Hydroxide | 1.03 |
| Anion Exchange Resin | 6.40 |
| LV HPMC | 6.80 |
| HV HPMC | 2.19 |
| Masking Flavor | 0.20 |
| Menthol | 0.41 |
| PEG-40 Hydrogenated Castor Oil | 0.10 |
| Sucralose | 0.16 |
| Ethanol | 30.17 |
| Purified Water | 46.33 |
| Total | 100.36 |

A vessel was charged with a solvent mixture containing about 46.33 g water and 30.17 g ethanol and about 6.47 g ketoprofen was subsequently added. The ketoprofen was mixed in the solvent mixture until dissolved, sonicated for 5 minutes and then mixed at 500 rpm. The pH of the ketoprofen/solvent mixture was adjusted using 1N NaOH to a pH of above 5.5, an amount of about 1.03 g, and mixed for 15 to 20 minutes. About 6.80 g DUOLITE® 1083 Cholestyramine anion exchange resin was added to the pH adjusted ketoprofen/solvent mixture, and the resulting composition was mixed for about 30 minutes for maximum binding. About 0.20 g masking flavor, about 0.10 g CREMOPHOR® ELP PEG-40 hydrogenated castor oil, about 0.41 g menthol, and about 0.16 g Sucralose were then added to the pH adjusted ketoprofen/solvent mixture/exchange resin composition and mixed at 500 rpm for 15 minutes. About 6.80 g PHARMACOAT® 603 HPMC and about 2.19 g METOLOSE® 60SH50 HPMC were added and the resulting composition mixed at 1,900 rpm for 30 minutes to form a coating solution. The coating solution was sonicated for 10 minutes. The sonicated coating solution was then formed into mono-layered wafers using a conventional coating technique. The average weight of each wafer was 66.30 mg (sd=7.03 mg) and the thickness was 112 μm (sd=6.2 μm). The wafer had no bitterness and/or throat irritation.

Example 3

Disintegrable oral films containing a taste masked ketoprofen were produced from the following ingredients:

| Component | Quantity (g) |
|---|---|
| Ketoprofen | 6.50 |
| Sodium Hydroxide | 1.36 |
| Anion Exchange Resin | 6.39 |
| LV HPMC | 6.80 |
| HV HPMC | 2.20 |
| Masking Flavor | 0.20 |
| Cherry Flavor | 0.20 |
| Polysorbate 80 | 0.20 |
| Menthol | 0.40 |
| Sucralose | 0.25 |
| Lysine Hydrochloride | 1.56 |
| Ethanol | 30.07 |
| Purified Water | 44.12 |
| Total | 100.25 |

A vessel was charged with a solvent mixture containing about 44.12 g water and 30.07 g ethanol and about 6.50 g ketoprofen was subsequently added to the solvent mixture. The ketoprofen/solvent mixture was mixed until dissolved, sonicated for 5 minutes and then mixed at 500 rpm. The pH of the ketoprofen/solvent mixture was then adjusted to a pH of above 5.5 using 1N NaOH, an amount of about 1.36 g, and mixed for about 10 minutes. About 6.50 g DUOLITE®

1083 Cholestyramine anion exchange resin was added to the pH adjusted ketoprofen/solvent mixture slowly under mixing for 30 minutes at 500 rpm. About 1.56 g lysine hydrochloride was added to the ketoprofen/solvent/exchange resin composition to stabilize the pH. About 0.20 g Masking Flavor, 0.20 g Cherry Flavor, about 0.20 g Polysorbate 80, about 0.40 g Menthol and about 0.25 g Sucralose were added to the pH stabilized composition and it was mixed at 500 rpm. About 6.80 g PHARMACOAT® 603 HPMC and about 2.20 g METOLOSE® 60SH50 HPMC were added and the resulting composition mixed at 1,900 rpm for 30 minutes to form a coating solution. The coating solution was sonicated for 10 minutes and de-aerated using an aspirator. The de-aerated coating solution was then formed into mono-layered wafers using a conventional coating technique The average weight of wafer was 55.15 mg (sd=1.75 mg) and thickness was 89 μm (d=3.2 μm). The resulting wafers had no bitterness and/or throat irritation.

Example 4

Disintegrable oral films containing a taste masked ketoprofen were produced from the following ingredients:

| Component | Quantity (g) |
| --- | --- |
| Ketoprofen | 6.48 |
| Sodium Hydroxide | 1.02 |
| Anion Exchange Resin | 6.39 |
| LV HPMC | 6.79 |
| HV HPMC | 2.21 |
| Masking Flavor | 0.21 |
| Lime Flavor | 0.16 |
| Polysorbate 80 | 0.15 |
| Menthol | 0.40 |
| PEG-40 Hydrogenated Castor Oil | 0.10 |
| Sucralose | 0.15 |
| Lysine Hydrate | 2.10 |
| Ethanol | 30.03 |
| Purified Water | 43.83 |
| Total | 100.02 |

A vessel was charged with a solvent mixture containing about 43.83 g water and about 30.03 g ethanol and about 6.38 g Ketoprofen was subsequently added. The ketoprofen/solvent mixture was mixed until dissolved, sonicated for 5 minutes and mixed at 500 rpm. The pH of the ketoprofen/solvent mixture was then adjusted to a pH of above 5.5 using 1N NaOH, an amount of about 1.02 g, and mixed for about IS minutes. About 6.39 g DUOLITE® 1093 Cholestyramine anion exchange resin was added to the pH adjusted ketoprofen/solvent mixture slowly under mixing for 30 minutes at 500 rpm. About 2.10 g Lysine Hydrate was added to the pH adjusted ketoprofen/solvent/exchange resin composition to stabilize the pH. About 0.21 g Masking Flavor, about 0.16 g Lime Flavor, about 0.10 g CREMOPHOR® RH 40 PEG-40 Hydrogenated Castor Oil, about 0.15 g Polysorbate 80, about 0.40 g Menthol, about 0.15 g Sucralose were added to the pH stabilized composition and mixed at 500 rpm. About 6.79 g PHARMACOAT® 603 HPMC and about 2.21 g METOLOSE® 60SH50 HPMC were added and the resulting composition mixed at 1,900 rpm for 30 minutes to form a coating solution. The coating solution was then sonicated for 10 minutes and do-aerated using an aspirator. The de-aerated coating solution was then formed into mono-layered wafers using a conventional coating technique. The average weight of wafer was 55.15 mg (sd=1.75 mg) and thickness was 89 μm (sd=3.2 μm). The wafers had no bitterness and throat irritation.

Example 5

Disintegrable oral films containing a taste masked ketoprofen were produced from the following ingredients:

| Component | Quantity (g) |
| --- | --- |
| Ketoprofen | 7.55 |
| Sodium Hydroxide | 1.19 |
| Anion exchange resin | 7.42 |
| LV HPMC | 6.86 |
| HV HPMC | 2.20 |
| Masking Flavor | 0.20 |
| Cherry Flavor | 0.46 |
| Polysorbate 80 | 0.22 |
| Menthol | 0.40 |
| PEG-40 Hydrogenated Castor Oil | 0.10 |
| Sucralose | 0.15 |
| Lysine Hydrate | 2.45 |
| Ethanol | 30.10 |
| Purified Water | 47.73 |
| Total | 107.03 |

A vessel was charged with a solvent mixture containing about 47.73 g water and about 30.10 g ethanol. About 7.55 g ketoprofen was added to the solvent mixture and mixed until dissolved, sonicated for 5 minutes and mixed at 500 rpm. The pH of the ketoprofen/solvent mixture was then adjusted to a pH of above 5.5 using 1N NaOH, an amount of about 1.19 g, and mixed for about 15 minutes. About 7.42 g DUOLITE® 1093 Cholestyramine anion exchange resin was added to the pH adjusted ketoprofen/solvent mixture slowly under mixing for 30 minutes at 500 rpm. About 2.45 g Lysine Hydrate was added to the ketoprofen/solvent/exchange resin mixture to stabilize the pH. About 0.20 g Masking Flavor, about 0.46 g Cherry Flavor, about 0.10 g CREMOPHOR® RH 40 PEG-40 Hydrogenated Castor Oil, about 0.22 g Polysorbate 80, about 0.40 g Menthol, and about 0.15 g Sucralose were added to the pH stabilized composition and mixed at 500 rpm. About 6.86 g PHARMACOAT® 603 HPMC and about 2.20 g METOLOSE® 60SH50 HPMC were added and the resulting composition mixed at 1,900 rpm for 30 minutes to form a coating solution. The coating solution was sonicated for about 10 minutes and de-aerated using an aspirator. The de-aerated coating solution was then formed into mono-layered wafers using a conventional coating technique. The average weight of wafer was 50.11 mg (sd=2.16 mg) and thickness was 68 μm (sd=3.9 μm). The resulting wafers had no bitterness and/or throat irritation.

Example 6

Disintegrable oral films containing a taste masked ketoprofen were produced from the following ingredients:

| Component | Quantity (g) |
| --- | --- |
| Ketoprofen | 6.47 |
| Sodium Hydroxide | 1.02 |
| Anion exchange resin | 6.39 |
| LV HPMC | 6.81 |
| HV HPMC | 2.22 |
| Masking Flavor | 0.20 |
| Lime Flavor | 0.15 |

-continued

| Component | Quantity (g) |
| --- | --- |
| Polysorbate 80 | 0.17 |
| Menthol | 0.40 |
| PEG-40 Hydrogenated Castor Oil | 0.10 |
| Sucralose | 0.15 |
| Ethanol | 30.14 |
| Purified Water | 45.90 |
| Total | 100.12 |

A vessel was charged with a solvent mixture containing about 45.90 g water and 30.14 g ethanol. About 6.47 g ketoprofen was added to the solvent mixture and mixed until dissolved, sonicated for 5 minutes and mixed at 500 rpm. The pH of the ketoprofen/solvent mixture was then adjusted to a pH of above 5.5 using 1N NaOH, an amount of about 1.02 g, and mixed for about IS minutes. About 6.39 g DUOLITE® 1093 Cholestyramine anion exchange resin was added to the pH adjusted ketoprofen/solvent mixture slowly under mixing for 30 minutes at 500 rpm. About 0.20 g Masking Flavor, about 0.15 g Lime Flavor, about 0.10 g CREMOPHOR® RH 40 PEG-40 Hydrogenated Castor Oil, about 0.17 g Polysorbate 80, about 0.40 g Menthol, and about 0.15 g Sucralose were added to the pH stabilized composition and mixed at 500 rpm. About 6.81 g PHARMACOAT® 603 HPMC and about 2.20 g METOLOSE® 60SH50 HPMC were added and the resulting composition mixed at 1,900 rpm for 30 minutes to form a coating solution. The coating solution was sonicated for about 10 minutes and de-aerated using an aspirator. The de-aerated coating solution was then formed into mono-layered wafers using a conventional coating technique. The average weight of water was 53.71 mg (sd=3.31 mg) and thickness was 81 µm (sd=3.9 µm). The resulting wafers had no bitterness and/or throat irritation.

Example 7

Disintegrable oral films containing a taste masked ketoprofen were produced from the following ingredients:

| Component | Quantity (g) |
| --- | --- |
| Ketoprofen | 6.51 |
| Anion exchange resin | 6.40 |
| LV HPMC | 6.50 |
| HV HPMC | 2.01 |
| Masking Flavor | 0.20 |
| Lime Flavor | 0.16 |
| Polysorbate 80 | 0.15 |
| Menthol | 0.40 |
| PEG-40 Hydrogenated Castor Oil | 0.10 |
| Sucralose | 0.16 |
| Lysine Hydrate | 4.20 |
| Purified Water | 73.27 |
| Total | 100.06 |

A vessel was charged with about 73.27 g water. About 4.2 g lysine hydrate were added and mixed at 500 rpm until dissolved. The pH of the lysine hydrate/water mixture was then adjusted to a pH of above 5.5 using Ketoprofen, an amount of about 6.51 g, and mixed for about 15 minutes. About 6.40 g DUOLITE® 1093 Cholestyramine anion exchange resin was added to the pH adjusted mixture slowly under mixing for 30 minutes at 500 rpm. About 0.20 g Masking Flavor, about 0.16 g Lime Flavor, about 0.10 g CREMOPHOR® RH 40 PEG-40 Hydrogenated Castor Oil, about 0.15 g Polysorbate 80, about 0.40 g Menthol, and about 0.16 g Sucralose were added to the composition and mixed at 500 rpm. About 6.50 g PHARMACOAT® 603 HPMC and about 2.01 g METOLOSE® 60SH50 HPMC were added and the resulting composition mixed at 1,900 rpm for 30 minutes to form a coating solution. The coating solution was sonicated for about 10 minutes and de-aerated using an aspirator. The de-aerated coating solution was then formed into mono-layered wafers using a conventional coating technique. The average weight of wafer was 59.71 mg (sd=1.67 mg) and thickness was 88 µm (sd=4.8 µm). The resulting wafers had no bitterness taste and/or throat irritation.

Example 8

Disintegrable oral films containing a taste masked ketoprofen were produced from the following ingredients:

| Component | Quantity (g) |
| --- | --- |
| Ketoprofen | 6.51 |
| Sodium Hydroxide | 1.54 |
| Anion exchange resin | 6.39 |
| LV HPMC | 6.50 |
| HV HPMC | 2.02 |
| Masking Flavor | 0.40 |
| Lime Flavor | 0.30 |
| Polysorbate 80 | 0.30 |
| Menthol | 0.40 |
| PEG-40 Hydrogenated Castor Oil | 0.30 |
| Sucralose | 0.30 |
| Lysine Hydrochloride | 2.34 |
| Purified Water | 72.82 |
| Total | 100.12 |

A vessel was charged with about 72.82 g water and about 1.5 g NaOH and mixed at 500 rpm. About 6.51 g ketoprofen was added slowly until the pH was above 5.5, mixed for 15 minutes, sonicated for 5 minutes, and 0.04 gm 1N NaOH added to bring the solution to a pH to 6.5 to 6.8. About 6.39 g DUOLITE® 1093 Cholestyramine anion exchange resin was added to the pH adjusted mixture slowly under mixing for 30 minutes at 500 rpm. About 2.34 g lysine hydrochloride was added in an equimolar amount to the 1N NaOH, an amount of about 2.34 g, was added to the solution. About 0.40 g Masking Flavor, about 0.30 g Lime Flavor, about 0.30 g CREMOPHOR® RH 40 PEG-40 Hydrogenated Castor Oil, about 0.30 g Polysorbate 80, about 0.40 g Menthol, and about 0.30 g Sucralose were added to the composition and mixed at 1,000 rpm. About 6.50 g PHARMACOAT® 603 HPMC and about 2.02 g METOLOSE® 60SH50 HPMC were added and the resulting composition mixed at 2,000 rpm for a minimum of 30 minutes to form a coating solution. The coating solution was sonicated for about 10 minutes and de-aerated using an aspirator. The de-aerated coating solution was then formed into mono-layered wafers using a conventional coating technique. The average weight of wafer was 64.38 mg (sd=2.44 mg) and thickness was 86 µm (sd=4.6 µm). This formulation produced a good film with good mechanical properties, particularly improved tear strength. The taste of the resulting wafers was good with no bitterness and/or throat irritation and/or burning sensation.

Example 9

Disintegrable oral films containing a taste masked ketoprofen were produced from the following ingredients:

| Component | Quantity (g) |
|---|---|
| Ketoprofen | 6.51 |
| Sodium Hydroxide | 1.02 |
| Anion exchange resin | 6.40 |
| LV HPMC | 6.51 |
| HV HPMC | 2.00 |
| Masking Flavor | 0.41 |
| Lime Flavor | 0.30 |
| Polysorbate 80 | 0.30 |
| Menthol | 0.41 |
| PEG-40 Hydrogenated Castor Oil | 0.80 |
| Sucralose | 0.30 |
| Lysine Hydrate | 2.11 |
| Purified Water | 73.40 |
| Total | 100.47 |

A vessel was charged with about 73.40 g water and about 25.60 g of 1N NaOH and mixed well. About 6.51 g of ketoprofen was added while stirring. The ketoprofen solution was then sonicated for 15 to 20 minutes until the ketoprofen was dissolved. About 0.4 gm NaOH added and the solution mixed at 500 rpm until the solution had a pH to 6.5 to 6.8. About 6.40 g DUOLITE® 1093 Cholestyramine anion exchange resin was added to the pH adjusted mixture slowly under mixing for 30 minutes at 500 rpm. About 2.11 g lysine hydrate was added. About 0.41 g Masking Flavor, about 0.30 g Lime Flavor, about 0.80 g CREMOPHOR® RH 40 PEG-40 Hydrogenated Castor Oil, about 0.30 g Polysorbate 80, about 0.41 g Menthol, and about 0.30 g Sucralose were added to the composition and mixed at 500 rpm. About 6.51 g PHARMACOAT® 603 HPMC and about 2.00 g METOLOSE® 60SH50 HPMC were added and the resulting composition mixed at 2,000 rpm for a minimum of 30 minutes to form a coating solution. The coating solution was sonicated for about 10 minutes and de-aerated using an aspirator. The de-aerated coating solution was then formed into mono-layered wafers using a conventional coating technique. The average weight of wafer was 53.63 mg (sd=3.14 mg) and thickness was 79 μm (sd=3.1 μm). The taste of the resulting wafers was good with no bitterness and/or throat irritation and/or burning sensation.

Example 10

Disintegrable oral films containing a taste masked ketoprofen were produced from the following ingredients:

| Component | Quantity (g) |
|---|---|
| Ketoprofen | 6.54 |
| Sodium Hydroxide | 1.07 |
| Anion exchange resin | 6.40 |
| LV HPMC | 6.50 |
| HV HPMC | 2.02 |
| Artificial Lime Flavor | 0.40 |
| Natural Lime Flavor | 0.31 |
| Polysorbate 80 | 0.29 |
| Menthol | 0.41 |
| PEG-40 Hydrogenated Castor Oil | 0.30 |
| Sucralose | 0.30 |
| Purified Water | 75.56 |
| Total | 100.10 |

A vessel was charged with about 75 g water and about 1 g sodium hydroxide and mixed at 400 rpm until all NaOH was dissolved. About 6.54 g ketoprofen was added, an the mixture was stirred at 400 rpm. About 6.40 g DUOLITE® 1093 Cholestyramine anion exchange resin was added slowly under mixing, and the resulting composition was mixed for about 20 minutes at 600 rpm, and then at 50 rpm for 50 minutes. About 0.30 g of sucralose and 0.40 of artificial lime flavor were added and the resulting mixture stirred at 400 rpm. Masking flavor, 0.31 g natural lime flavor, 030 g CREMOPHOR® RH 40 PEG-40 hydrogenated castor oil, about 0.29 g Polysorbate 80, and about 0.41 menthol premix were then added and mixed at 600 rpm for several minutes and then the mixing speed was increased to 1,000 rpm and the composition was mixed until uniform. A premix containing about 6.50 g PHARMACOAT® 603 HPMC and about 2.02 g METOLOSE® 60SH50 HPMC was then added and the resulting composition mixed at 350 rpm, and after fully charging the polymer, the speed was reduced to 200 rpm until the HPMC was dissolved, resulting in a coating solution. The coating solution was then formed into mono-layered wafers using a conventional coating technique. The average weight of the wafers was 47.24 mg (sd=2.88 mg) and thickness was 80 μm (sd=2.7 μm). The taste of the resulting wafers was good without bitterness and/or throat irritation.

Example 11

Disintegrable oral films containing a taste masked ketoprofen were produced from the following ingredients:

| Component | Quantity (g) |
|---|---|
| Ketoprofen | 6.51 |
| Sodium Hydroxide | 1.08 |
| Anion exchange resin | 6.42 |
| LV HPMC | 6.54 |
| HV HPMC | 2.49 |
| Art. Lime Flavor-53 | 0.41 |
| Nat. Lime Flavor | 0.31 |
| Polysorbate 80 | 0.37 |
| Menthol | 0.42 |
| PEG-40 Hydrogenated Castor Oil | 0.45 |
| Sucralose | 0.30 |
| Lysine Hydrate | 0.90 |
| Purified Water | 74.74 |
| Total | 100.94 |

A vessel was charged with about 74.74 g water and about 1.08 g sodium hydroxide and mixed at 400 rpm until all NaOH was dissolved. About 6.51 g ketoprofen was added slowly, an the mixture was stirred at 400 rpm, until the pH was above 5.5. About 6.42 g DUOLITE® 1093 Cholestyramine anion exchange resin was added slowly under mixing, and the resulting composition was mixed for about 30 minutes at 600 rpm. About 0.90 g lysine hydrate, 0.30 g of sucralose and 0.41 of artificial lime flavor No. 53 were added and the resulting mixture stirred at 400 rpm for about 10 minutes. A premix containing about 0.31 g natural lime flavor, 0.45 g CREMOPHOR® RH 40 PEG-40 hydrogenated castor oil, about 0.37 g Polysorbate 80, and about 0.42 menthol was then added and mixed at 600 rpm for 30 minutes, after which the mixing speed was increased to 1,000 rpm and the composition was mixed until uniform. A premix containing about 6.54 g PHARMACOAT® 603 HPMC and about 2.49 g METOLOSE® 60SH50 HPMC was then added and the resulting composition mixed at 250 to 400 rpm, and after fully charging the polymer, the speed was reduced to 200 rpm until the HPMC was dissolved, resulting in a coating solution. The coating solution was subsequently de-gassed. The de-gassed coating solution was formed into mono-layered wafers using a conventional coating technique. The average weight of wafer was 50.78 mg (sd=1.77 mg) and thickness was 67 μm (sd=2.5 μm). The taste of the resulting wafers was good without bitterness and/or irritation.

Example 12

Disintegrable oral films containing a taste masked ketoprofen were produced from the following ingredients:

| Component | Quantity (g) |
| --- | --- |
| Ketoprofen | 6.51 |
| Sodium Hydroxide | 1.08 |
| Anion exchange resin | 6.48 |
| LV HPMC | 6.59 |
| HV HPMC | 2.01 |
| Masking Flavor | 0.41 |
| Nat. Lime Flavor | 0.30 |
| Polysorbate 80 | 0.30 |
| Menthol | 0.42 |
| PEG-40 Hydrogenated Castor Oil | 0.34 |
| Sucralose | 0.32 |
| Purified Water | 75.57 |
| Total | 100.33 |

A vessel was charged with about 75.57 g water and about 1.08 g sodium hydroxide and mixed at 400 rpm until all NaOH was dissolved. About 6.51 g ketoprofen was added slowly, an the mixture was stirred at 400 rpm until the pH was above 5.5. About 6.48 g DUOLITE® 1093 Cholestyramine anion exchange resin was added slowly under mixing, and the resulting composition was mixed for about 30 minutes at 600 rpm. About 0.32 g of sucralose, about 0.41 g Masking flavor, about 0.30 g of artificial lime flavor, 0.34 g CREMOPHOR® RH 40 PEG-40 hydrogenated castor oil, about 0.30 g Polysorbate 80, and about 0.42 menthol was then added and mixed at 600 rpm for 30 minutes, after which the mixing speed was increased to 1,000 rpm and the composition was mixed until uniform. A premix containing about 6.59 g PHARMACOAT® 603 HPMC and about 2.01 g METOLOSE® 60SH50 HPMC was then added and the resulting composition mixed at 250 to 400 rpm, and after fully charging the polymer, the speed was reduced to 200 rpm until the HPMC was dissolved, resulting in a coating solution. The coating solution was gently stirred prior to wafer formation, and the stirred coating solution was formed into mono-layered wafers using a conventional coating technique. The average weight of the resulting wafers was 51.11 mg (sd=1.05 mg) and thickness was 75 μm (sd=3.5 μm). The taste of the resulting wafers was good without bitterness and/or irritation.

Example 13

Disintegrable oral films containing a taste masked ketoprofen were produced from the following ingredients:

| Component | Quantity (g) |
| --- | --- |
| Ketoprofen | 6.52 |
| Sodium Hydroxide | 1.54 |
| Anion exchange resin | 6.39 |
| LV HPMC | 6.53 |
| HV HPMC | 2.02 |
| Masking Flavor | 0.40 |
| Art. Tutti Frutti | 0.63 |
| Polysorbate 80 | 0.33 |
| Menthol | 0.42 |
| PEG-40 Hydrogenated Castor Oil | 0.30 |
| Sucralose | 0.30 |
| Lysine Hydrochloride | 2.34 |
| Purified Water | 72.96 |
| Total | 100.68 |

A vessel was charged with about 72.96 g water and about 1.54 g sodium hydroxide and mixed at 500 rpm. About 6.52 g ketoprofen was added slowly, an the mixture was stirred for 15 minutes until the pH was above 5.5, and sonicated for 5 minutes. About 6.39 g DUOLITE® 1093 Cholestyramine anion exchange resin was added slowly under mixing, and the resulting composition was mixed for about 30 minutes at 600 rpm. About 2.34 g Lysine Hydrochloride was weighed and added equimolar to the 1N NaOH, mixed until dissolved into solution, and the resulting solution added to the mixture. A premix containing about 0.30 g of sucralose, about 0.40 g Masking flavor, about 0.63 g of artificial tutti fruitti flavor, 0.30 g CREMOPHOR® RH 40 PEG-40 hydrogenated castor oil, about 0.33 g Polysorbate 80, and about 0.42 menthol was then added and mixed at 1,000 rpm. A premix containing about 6.53 g PHARMACOAT® 603 HPMC and about 2.02 g METOLOSE® 60SH50 HPMC was then added and the resulting composition mixed at 2000 rpm for a minimum of 30 minutes, resulting in a coating solution. The coating solution was subsequently sonicated for 10 minutes and de-aerated using an aspirator. The de-aerated coating solution was formed into mono-layered wafers using a conventional coating technique. The average weight of the resulting wafers was 60.66 mg (sd=1.82 mg) and thickness was 83 μm (sd=3.2 μm). The resulting wafers had no bitterness taste and/or throat irritation.

Example 14

Disintegrable oral films containing a taste masked ketoprofen were produced from the following ingredients:

| Component | Quantity (g) |
| --- | --- |
| Ketoprofen | 10.59 |
| HV HPMC | 3.20 |
| LV HPMC | 9.72 |
| NaOH | 1.66 |
| Anion exchange resin | 10.32 |
| Sucralose | 0.36 |
| Isomalt | 1.52 |
| Menthol | 0.84 |
| Peppermint Flavor | 1.21 |
| Polysorbate 80 | 0.27 |
| PEG-40 Hydrogenated Castor Oil | 0.57 |
| Purified Water | 109.74 |
| Total | 150.00 |

A vessel was charged with about 109.74 g water and about 10% NaOH solution and mixed at 500 rpm to insure homogeneity. About 10.59 g ketoprofen was added slowly, an the mixture was stirred at 500 rpm for about 30 minutes until the pH was above 5.5, and sonicated for 10 minutes until the solution was clear. About 10.32 g DUOLITE® 1093 Cholestyramine anion exchange resin was added slowly under mixing, and the resulting composition was mixed for about 30 minutes at 500 rpm. About 0.36 g of sucralose, about 1.52 g ISOMALTIDEX® isomalt were added and stirred into the mixture. A premix containing about 1.21 g of peppermint flavor, 0.57 g CREMOPHOR® RH 40 PEG-40 hydrogenated castor oil, about 0.27 g Polysorbate 80, and about 0.84 g menthol was made in a separate beaker and this flavor premix was added and mixed to the main formulation mixture and stirred at 800 rpm for 1 hour. A premix containing about 9.72 g PHARMACOAT® 603 HPMC and about 32 g METOLOSE® 60SH50 HPMC was then added and the resulting composition mixed at 800 rpm for 1 hour, resulting in a coating solution. The coating solution was subsequently de-aerated using vacuum. The do-aerated coating solution was formed into mono-layered wafers using a conventional coating technique. The resulting wafers had an average weight of 52.34 mg (SD-1.44 mg). The taste of the resulting wafers was good without bitterness and/or throat irritation.

Example 15

Disintegrable oral films containing a taste masked ketoprofen were produced from the following ingredients:

| Component | Quantity (g) |
| --- | --- |
| Ketoprofen | 10.59 |
| HV HPMC | 3.20 |
| LV HPMC | 9.72 |
| NaOH | 1.66 |
| Anion exchange resin | 10.32 |
| Sucralose | 0.36 |
| Isomalt | 1.52 |
| Menthol | 0.84 |
| Spearmint Flavor | 1.21 |
| Polysorbate 80 | 0.27 |
| PEG-40 Hydrogenated Castor Oil | 0.57 |
| Purified Water | 109.74 |
| Total | 150.00 |

A vessel was charged with about 109.74 g water and about 10% NaOH solution and mixed at 500 rpm to insure homogeneity. About 10.59 g ketoprofen was added slowly, an the mixture was stirred at 500 rpm for about 30 minutes until the pH was above 5.5, and sonicated for 10 minutes until the solution was clear. About 10.32 g DUOLITE®1093 Cholestyramine anion exchange resin was added slowly under mixing, and the resulting composition was mixed for about 30 minutes at 500 rpm. About 0.36 g of sucralose, about 1.52 g ISOMALTIDEX® isomalt were added and stirred into the mixture. A premix containing about 1.21 g of spearmint flavor, 0.57 g CREMOPHOR® RH 40 PEG-40 hydrogenated castor oil, about 0.27 g Polysorbate 80, and about 0.84 g menthol was made in a separate beaker and this flavor premix was admixed into the main formulation mixture and stirred at 800 rpm for 30 minutes. A premix containing about 9.72 g PHARMACOAT® 603 HPMC and about 3.20 g METOLOSE® 60SH50 HPMC was then added and the resulting composition mixed at 800 rpm for 1 hour, resulting in a coating solution. The coating solution was subsequently de-aerated using vacuum. The do-aerated coating solution was formed into mono-layered wafers using a conventional coating technique. The taste of the resulting wafers was good without bitterness and/or throat irritation.

Example 16

Disintegrable oral films containing a taste masked ketoprofen were produced from the following ingredients:

| Component | Quantity (g) |
| --- | --- |
| Ketoprofen | 10.33 |
| NaOH | 1.62 |
| Anion exchange resin | 10.07 |
| LV HPMC | 9.48 |
| HV HPMC | 3.13 |
| Peppermint Flavor | 0.93 |
| Polysorbate 80 | 0.26 |
| Menthol | 0.82 |
| PEG-40 Hydrogenated Castor Oil | 0.56 |
| Sucralose | 0.35 |
| Isomaltidex | 1.49 |
| Methylsalicylate | 1.24 |
| Purified Water | 109.74 |
| Total | 150.02 |

A vessel was charged with about 109.74 g water and about 10% NaOH solution and mixed at 500 rpm to insure homogeneity. About 10.33 g ketoprofen was added slowly, an the mixture was stirred at 500 rpm for about 30 minutes until the pH was above 5.5, and sonicated for 10 minutes until the solution was clear. About 10.07 g DUOLITE® 1093 Cholestyramine anion exchange resin was added slowly under mixing, and the resulting composition was mixed for about 30 minutes at 500 rpm. About 0.35 g of sucralose and about 1.49 g ISOMALTIDEX® isomalt were added and stirred into the mixture. A premix containing about 0.93 g of peppermint flavor, 0.56 g CREMOPHOR® RH 40 PEG-40 hydrogenated castor oil, about 0.26 g Polysorbate 80, about 1.24 g methylsalicylate and about 0.82 g menthol was made in a separate beaker and this flavor premix was admixed into the main formulation mixture and stirred at 800 rpm for 1 hour. A premix containing about 9.48 g PHARMACOAT® 603 HPMC and about 3.13 g METOLOSE® 60SH50 HPMC was then added and the resulting composition mixed at 800 rpm for 1 hour, resulting in a coating solution. The coating solution was subsequently de-aerated using vacuum. The de-aerated coating solution was formed into mono-layered wafers using a conventional coating technique. The taste of the resulting wafers was good without bitterness and/or throat irritation.

HPC/HPMC Formulations

Example 17

Disintegrable oral films containing a taste masked ketoprofen were produced from the following ingredients:

| Component | Quantity (g) |
| --- | --- |
| Ketoprofen | 7.02 |
| Sodium Hydroxide | 1.10 |
| Anion exchange resin | 6.91 |
| HPC | 6.04 |
| HV HPMC | 2.01 |
| Lime Flavor | 0.31 |
| Polysorbate 80 | 0.19 |
| Menthol | 0.40 |
| PEG-40 Hydrogenated Castor Oil | 0.10 |
| Sucralose | 0.15 |
| Lysine Hydrate | 2.27 |
| Purified Water | 74.52 |
| Total | 101.02 |

A vessel was charged with about 74.52 g water and about 7.02 g ketoprofen and sonicated for about 10 minutes. 1 N NaOH was added until the pH was above 5.5, an amount of about 1.10 g, and mixed for 15 to 20 minutes. About 10.07 g DUOLITE® 1093 Cholestyramine anion exchange resin was added under mixing, and the resulting composition was mixed for about 30 minutes at 500 rpm. About 2.27 g lysine hydrate was added to control the pH. About 0.15 g of sucralose, about 0.31 g of lime flavor, about 0.10 g CREMOPHOR® RH 40 PEG-40 hydrogenated castor oil, about 0.19 g Polysorbate 80, about 0.40 g menthol was admixed into the main formulation mixture and stirred at 500 rpm for 15 minutes. About 6.04 KLUCEL® LF hydroxypropylcellulose ("HPC"), commercially available from Hercules of Inc. of Wilmington, Del., and about 2.01 g METOLOSE® 60SH50 HPMC was then added and the resulting composition mixed at 1900 rpm for 30 minutes, resulting in a coating solution. The coating solution was subsequently sonicated for 10 minutes and de-aerated using an aspirator. The de-aerated coating solution was formed into mono-layered wafers using a conventional coating technique. The average weight of the wafers was 54.68 mg (sd=2.07 mg) and thickness was 79 μm (sd=2.5 μm). The resulting wafers had no bitterness and/or throat irritation.

Example 18

Disintegrable oral films containing a taste masked ketoprofen were produced from the following ingredients:

| Component | Quantity (g) |
| --- | --- |
| Ketoprofen | 7.05 |
| Sodium Hydroxide | 1.11 |
| Anion exchange resin | 6.93 |
| HPC | 6.02 |
| HV HPMC | 2.03 |
| Lime Flavor | 0.31 |
| Polysorbate 80 | 0.21 |
| Menthol | 0.41 |
| PEG-40 Hydrogenated Castor Oil | 0.13 |
| Sucralose | 0.16 |
| Purified Water | 74.65 |
| Total | 99.01 |

A vessel was charged with about 74.65 g water and about 7.05 g ketoprofen and sonicated for about 10 minutes. 1 N NaOH was added until the pH was above 5.5, an amount of about 1.11 g, and mixed for 15 to 20 minutes. About 6.93 g DUOLITE® 1093 Cholestyramine anion exchange resin was added under mixing, and the resulting composition was mixed for about 30 minutes at 500 rpm. About 0.16 g of sucralose, about 0.31 g of lime flavor, about 0.13 g CREMOPHOR® RH 40 PEG-40 hydrogenated castor oil, about 0.21 g Polysorbate 80, about 0.41 g menthol was admixed into the main formulation mixture and stirred at 500 rpm for IS minutes. About 6.02 KLUCEL® LF HPC and about 2.03 g METOLOSE® 60SH50 HPMC was then added and the resulting composition mixed at 1900 rpm for 30 minutes, resulting in a coating solution. The coating solution was subsequently sonicated for 10 minutes and dc-aerated using an aspirator. The de-aerated coating solution was formed into mono-layered wafers using a conventional coating technique. The average weight of wafer was 53.72 mg (sd=0.85 mg) and thickness was 75 μm (sd=2.9 μm). The resulting wafers had a taste that was good without bitterness and/or throat irritation.

Example 19

Disintegrable oral films containing a taste masked ketoprofen were produced from the following ingredients:

| Component | Quantity (g) |
| --- | --- |
| Ketoprofen | 6.54 |
| Anion exchange resin | 6.43 |
| HPC | 6.00 |
| HV HPMC | 2.01 |
| Lime Flavor | 0.31 |
| Polysorbate 80 | 0.22 |
| Menthol | 0.40 |
| PEG-40 Hydrogenated Castor Oil | 0.10 |
| Sucralose | 0.16 |
| Purified Water | 73.84 |
| Total | 100.26 |

A vessel was charged with about 73.84 g water and lysine hydrate and mixed at 500 rpm. About 6.54 g ketoprofen was added slowly until the pH was above 5.5, and mixed for 15 minutes. About 6.43 g DUOLITE® 1093 Cholestyramine anion exchange resin was added slowly under mixing, and the resulting composition was mixed for about 30 minutes at 500 rpm. A premix containing about 0.31 g of lime flavor, 0.10 g CREMOPHOR® RH 44 PEG-40 hydrogenated castor oil, about 0.22 g Polysorbate 80, and about 0.40 g menthol was made in a separate beaker and this flavor premix was admixed into the main formulation mixture. About 0.16 g sucralose was added and the mixture stirred at 500 rpm for 15 minutes. About 2.01 g METOLOSE® 60SH50 HPMC and about 6.00 g KLUCEL® LF HPC were then added and the resulting composition mixed at 1.900 rpm for 30 minutes, resulting in a coating solution. The coating solution was subsequently de-aerated using an aspirator and sonicated for 10 minutes. The coating solution was formed into mono-layered wafers using a conventional coating technique. The average weight of wafer was 57.68 mg (sd=1.22 mg) and thickness was 79 μm (sd=3.1 μm). The taste of the resulting wafers was good without bitterness and/or throat irritation.

Sodium CMC/HPMC Formulations

Example 20

Disintegrable oral films containing a taste masked ketoprofen were produced from the following ingredients:

| Component | Quantity (g) |
| --- | --- |
| Ketoprofen | 7.14 |
| Anion exchange resin | 3.50 |
| CMC | 9.14 |
| Lime Flavor | 0.24 |
| Polysorbate 80 | 0.10 |
| Ethanol | 50.01 |
| Purified Water | 84.02 |
| Total | 154.15 |

A vessel was charged with about 84.02 g water, about 50.01 g ethanol, about 7.14 g ketoprofen and 3.50 g DUOLITE® 1083 Cholestyramine anion exchange resin, and the resulting composition was sonicated for about 30 minutes. About 0.24 g of lime flavor and about 0.10 g Polysorbate 80 were added, and the mixture sonicated for 10 minutes. About 9.14 g of AQUALON® CMC-7LF sodium carboxymethyl cellulose ("CMC"), a cellulose gum commercially available from Ashland Chemical Company of Kentucky was then added and the resulting composition stirred at 400 rpm for 15 minutes, after which the stir speed was increased to 1900 rpm for 30 minutes, resulting in a coating solution. The coating solution was subsequently do-aerated using an aspirator and sonicated for 15 minutes. The coating solution was formed into mono-layered wafers using a conventional coating technique.

Example 21

Disintegrable oral films containing a taste masked ketoprofen were produced from the following ingredients:

| Component | Quantity (g) |
|---|---|
| Ketoprofen | 6.50 |
| Sodium Hydroxide | 1.53 |
| Anion exchange resin | 6.39 |
| CMC | 6.83 |
| HV HPMC | 2.23 |
| Lime Flavor | 0.23 |
| Polysorbate 80 | 0.19 |
| Menthol | 0.42 |
| PEG-40 Hydrogenated Castor Oil | 0.12 |
| Isomalt | 1.07 |
| Purified Water | 75.21 |
| Total | 100.10 |

A vessel was charged with about 75.21 g water and about 6.50 g ketoprofen. The resulting composition was mixed at 500 rpm to form a uniform suspension. The pH was adjusted by adding 1N NaOH until the pH was above 5.5, an amount of about 1.52 g, and mixing for about 15 to 20 minutes. About 6.39 g DUOLITE® 1083 Cholestyramine anion exchange resin was added under mixing and the resulting composition was mixed for about 30 minutes at 500 rpm. About 0.23 g of lime flavor, about 0.19 g Polysorbate 80, about 0.42 g menthol, about 1.07 g isomalt and about 0.12 g CREMOPHOR® ELP PEG-40 Hydrogenated castor oil were added. About 6.83 g of AQUALON® CMC-7LF sodium CMC and about 2.23 g METOLOSE® 60SH50 HPMC were added and the resulting composition stirred at 1900 rpm for 30 minutes, resulting in a coating solution. The coating solution was subsequently sonicated for 10 minutes. The sonicated coating solution was formed into mono-layered wafers using a conventional coating technique. The average weight of the resulting wafer was 47.93 mg (sd=0.54 mg) and thickness was 79 µm (sd=2.4 µm). The taste of the resulting wafers was good without bitterness and/or throat irritation.

Example 22

Disintegrable oral films containing a taste masked ketoprofen were produced from the following ingredients:

| Component | Quantity (g) |
|---|---|
| Ketoprofen | 6.51 |
| Sodium Hydroxide | 1.54 |
| Anion exchange resin | 6.40 |
| CMC | 6.81 |
| HV HPMC | 2.22 |
| Cherry Flavor | 0.41 |
| Polysorbate 80 | 0.21 |
| Menthol | 0.41 |
| PEG-40 Hydrogenated Castor Oil | 0.12 |
| Sucralose | 0.18 |
| Isomaltidex | 1.09 |
| Lysine Hydrochloride | 2.34 |
| Ethanol | 10.05 |
| Purified Water | 96.93 |
| Total | 135.21 |

A vessel was charged with about 96.93 g water, about 10.05 g ethanol and about 6.51 g ketoprofen. The resulting composition was mixed at 500 rpm to form a uniform suspension. The pH was adjusted by adding 1 N NaOH until the pH was above 5.5, an amount of about 1.54 g, and mixing for about 15 to 20 minutes. About 6.40 g DUOLITE® 1083 Cholestyramine anion exchange resin was added under mixing and the resulting composition was mixed for about 30 minutes at 500 rpm. In a separate beaker, about 2.34 g Lysine Hydrochloride in an equimolar amount to 1N NaOH until a clear solution was formed. This Lysine hydrochloride solution was added to the mixture. About 0.41 g Cherry flavor, about 0.21 g Polysorbate 80, about 0.41 g menthol, about 1.09 g isomalt and about 0.12 g CREMOPHOR® ELP PEG-40 Hydrogenated castor oil were added and the resulting mixture stirred at 1,900 rpm for 30 minutes. About 6.81 g of AQUALON® CMC-7LF sodium CMC and about 2.22 g METOLOSE® 60SH50 HPMC were added and the resulting composition stirred at 1,900 rpm for 30 minutes, resulting in a coating solution. The coating solution was subsequently sonicated for 10 minutes. The sonicated coating solution was formed into mono-layered wafers using a conventional coating technique. The average weight of wafer was 70.71 mg (sd=1.50 mg) and thickness was 94 µm (sd=4.0 µm). The resulting film had good mechanical properties, particularly improved tear strength, with pleasant cooling taste and no bitterness and/or throat irritation.

Example 23

Disintegrable oral films containing a taste masked ketoprofen were produced from the following ingredients:

| Component | Quantity (g) |
|---|---|
| Ketoprofen | 6.54 |
| Sodium Hydroxide | 1.03 |
| Anion exchange resin | 6.43 |
| CMC | 6.84 |
| HV HPMC | 2.24 |
| Cherry Flavor | 0.41 |
| Polysorbate 80 | 0.22 |
| Menthol | 0.40 |
| PEG-40 Hydrogenated Castor Oil | 0.12 |
| Sucralose | 0.17 |
| Isomalt | 1.07 |
| Lysine Hydrate | 2.11 |
| Ethanol | 10.03 |
| Purified Water | 97.54 |
| Total | 135.15 |

A vessel was charged with about 97.54 g water, about 10.03 g ethanol and about 6.54 g ketoprofen, and the resulting composition was mixed at 500 rpm to form a uniform suspension. The pH was adjusted by adding 1N NaOH until the pH was above 5.5, an amount of about 1.03 g, and mixing for about 15 to 20 minutes. About 6.43 g DUOLITE® 1083 Cholestyramine anion exchange resin was added under mixing and the resulting composition was mixed for about 30 minutes at 500 rpm. About 2.11 g Lysine Hydrochloride was added to the mixture to further stabilize the pH. About 0.41 g Cherry flavor, about 0.22 g Polysorbate 80, about 0.40 g menthol, about 1.07 g isomalt and about 0.12 g CREMOPHOR® ELP PEG-40 Hydrogenated castor oil were added and the resulting mixture stirred at 500 rpm for 15 minutes. About 6.84 g of AQUALON® CMC-7LF sodium CMC and about 2.24 g METOLOSE® 60SH50 HPMC were added and the resulting composition stirred at 1,900 rpm for 30 minutes, resulting in a coating solution. The coating solution was subsequently sonicated for 10 minutes and do-aerated using an aspirator. The de-aerated coating solution was formed into mono-layered wafers using a conventional coating technique The average weight of the resulting wafers was 48.87 mg (sd=0.93 mg) and thickness was 75 μm (sd=3.1 μm). This formulation produced a clear film with good mechanical properties, particularly good tear strength, without bitterness and/or throat irritation.

Example 24

Disintegrable oral films containing a taste masked ketoprofen were produced from the following ingredients:

| Component | Quantity (g) |
|---|---|
| Ketoprofen | 7.01 |
| Sodium Hydroxide | 1.10 |
| Anion exchange resin | 6.89 |
| CMC | 6.50 |
| HV HPMC | 2.02 |
| Cherry Flavor | 0.42 |
| Polysorbate 80 | 0.19 |
| Menthol | 0.40 |
| PEG-40 Hydrogenated Castor Oil | 0.10 |
| Sucralose | 0.15 |
| Isomalt | 1.02 |
| Lysine Hydrate | 2.27 |
| Ethanol | 30.04 |
| Purified Water | 46.53 |
| Total | 104.64 |

A vessel was charged with about 46.53 g water, about 30.04 g ethanol and about 7.01 g ketoprofen. The resulting composition was mixed at 500 rpm to form a uniform suspension. The pH was adjusted by adding 1N NaOH until the pH was above 5.5, an amount of about 1.10 g, and mixing for about 15 minutes. About 6.89 g DUOLITE® 1093 Cholestyramine anion exchange resin was added under mixing and the resulting composition was mixed for about 30 minutes at 500 rpm. About 2.27 g Lysine Hydrochloride was added to further stabilize the pH. About 0.42 g Cherry flavor, about 0.19 g Polysorbate 80, about 0.40 g menthol, about 1.02 g isomalt and about 0.10 g CREMOPHOR® RH40 PEG-40 Hydrogenated castor oil were added and the resulting mixture stirred at 1,900 rpm for 30 minutes. About 6.50 g of AQUALON® CMC-7LF sodium CMC cellulose gum and about 2.02 g METOLOSE® 60SH50 HPMC were added and the resulting composition stirred at 1,900 rpm for 30 minutes, resulting in a coating solution. The coating solution was subsequently sonicated for 10 minutes. The sonicated coating solution was formed into mono-layered wafers using a conventional coating technique. The average weight of the resulting wafers was 54.68 mg (sd=2.07 mg) and the thickness was 79 μm (sd=2.5 μm). The taste of the resulting wafers was good with no bitterness and/or throat irritation.

Example 25

Disintegrable oral films containing a taste masked ketoprofen were produced from the following ingredients:

| Component | Quantity (g) |
|---|---|
| Ketoprofen | 7.05 |
| Sodium Hydroxide | 1.11 |
| Anion exchange resin | 6.90 |
| CMC | 6.51 |
| HV HPMC | 2.05 |
| Lime Flavor | 0.30 |
| Polysorbate 80 | 0.19 |
| Menthol | 0.40 |
| PEG-40 Hydrogenated Castor Oil | 0.11 |
| Sucralose | 0.17 |
| Isomaltidex | 1.01 |
| Ethanol | 30.01 |
| Purified Water | 46.67 |
| Total | 102.5 |

A vessel was charged with about 46.67 g water, about 30.01 g ethanol and about 7.05 g ketoprofen. The resulting composition was mixed at 500 rpm for 15 to 20 minutes to form a uniform suspension. The pH was adjusted by adding 1N NaOH until the pH was above 5.5, an amount of about 1.11 g, and the solution mixed for about 15 to 20 minutes at 500 rpm. About 6.90 g DUOLITE® 1093 Cholestyramine anion exchange resin was added under mixing and the resulting composition was mixed for about 30 minutes at 500 rpm. A premixture containing about 0.30 g lime flavor, about 0.19 g Polysorbate 80, and about 0.11 g CREMOPHOR® RH40 PEG-40 Hydrogenated castor oil was added and the resulting mixture stirred at 500 rpm. A premix containing about 0.40 g menthol, about 0.17 g sucralose and about 1.01 g isomalt was added and the resulting mixture stirred at 500 rpm for 30 minutes. A premix containing bout 6.31 g of AQUALON® CMC-7LF sodium CMC cellulose gum and about 2.05 g METOLOSE® 60SH50 HPMC was added and the resulting composition stirred at 1,900 rpm for 30 minutes, resulting in a coating solution. The coating solution was de-aerated using sonication and low vacuum. The do-aerated coating solution was formed into mono-layered wafers using a conventional coating technique. The average weight of the resulting wafers was 60.05 mg (sd=1.35 mg) and the thickness was 83 μm (sd=2.2 μm). The film had good mechanical properties. The resulting wafers tasted good without bitterness, burning and/or throat irritation.

Example 26

Disintegrable oral films containing a taste masked ketoprofen were produced from the following ingredients:

| Component | Quantity (g) |
|---|---|
| Ketoprofen | 5.53 |
| Sodium Hydroxide | 0.85 |
| Anion exchange resin | 5.41 |
| CMC | 5.10 |
| HV HPMC | 1.63 |
| Lime Flavor | 0.26 |
| Polysorbate 80 | 0.13 |
| Menthol | 0.32 |
| PEG-40 Hydrogenated Castor Oil | 0.08 |
| Sucralose | 0.16 |

| Component | Quantity (g) |
| --- | --- |
| Isomalt | 0.84 |
| Purified Water | 75.84 |
| Total | 96.15 |

A vessel was charged with about 65.84 g water, about 0.85 g NaOH. Subsequently, ketoprofen was added until the pH was above 5.5, an amount of about 5.53 g. About 5.41 g DUOLITE® 1093 Cholestyramine anion exchange resin was added under mixing and the resulting composition was mixed for about 40 minutes at 400 rpm. A flavor premixture containing about 0.26 g lime flavor, about 0.13 g Polysorbate 80, and about 0.08 g CREMOPHOR® RH40 PEG-40 Hydrogenated castor oil and 0.32 g menthol was formed in a separate beaker and mixed until the methanol dissolved, was added and the resulting mixture stirred at 500 rpm. The flavor premix was then added to the ketoprofen mixture and the resulting mixture stirred for 15 minutes at 300 rpm. About 0.16 g sucralose and about 0.84 g isomalt were added and the resulting mixture stirred at 300 rpm for 15 minutes. A premix containing about 5.10 g of AQUALON® CMC-7LF sodium CMC and about 1.63 g METOLOSE® 60SH50 HPMC was added. After addition of the film forming polymer premix, the stirring was stopped and the mixture was allowed to degas for 30 minutes. This de-gassed coating solution was formed into mono-layered waters using a conventional coating technique. The average weight of wafer was 39.98 mg (sd=0.68 mg) and thickness was 68 μm (sd=2.5 μm). The film had good mechanical properties. The resulting wafers dissolved quickly in the mouth, and the wafer taste was good without bitterness and/or throat irritation.

Example 27

Disintegrable oral films containing a taste masked ketoprofen were produced from the following ingredients:

| Component | Quantity (g) |
| --- | --- |
| Ketoprofen | 6.52 |
| Anion exchange resin | 6.41 |
| CMC | 5.55 |
| HV HPMC | 1.75 |
| Lime Flavor | 0.31 |
| Polysorbate 80 | 0.21 |
| Menthol | 0.40 |
| PEG-40 Hydrogenated Castor Oil | 0.14 |
| Sucralose | 0.16 |
| Isomalt | 1.04 |
| Lysine Hydrate | 4.21 |
| Purified Water | 73.56 |
| Total | 100.26 |

A vessel was charged with about 73.56 g water and then about 4.21 g lysine hydrate. This composition was mixed until dissolved and then mixed at 500 rpm. Ketoprofen was added slowly until the pH was above 5.5, an amount of about 6.52 g, and mixed for 15 minutes. About 6.41 g DUOLITE® 1093 Cholestyramine anion exchange resin was added under mixing and the resulting composition was mixed for about 30 minutes at 500 rpm. A flavor premixture containing about 0.31 g lime flavor, about 0.21 g Polysorbate 80, and about 0.14 g CREMOPHOR® RH40 PEG-40 Hydrogenated castor oil and 0.40 g menthol was formed in a separate beaker and mixed until the menthol dissolved. The flavor premixture was added to the ketoprofen mixture and the resulting mixture stirred. About 0.16 g sucralose and about 1.04 g isomalt were added and the resulting mixture stirred at 500 rpm for 15 min. About 5.55 g of AQUALON® CMC-7LF Sodium CMC and about 1.75 g METOLOSE® 60SH50 HPMC was added and the resulting composition was mixed at 1,900 rpm for 30 minutes. The composition was then sonicated for 10 minutes and de-aerated using an aspirator. The aspirated coating solution was formed into mono-layered wafers using a conventional coating technique. The average weight of wafer was 61.70 mg (sd=0.64 mg) and thickness was 82 μm (sd=3.1 μm). The film had good mechanical properties, especially improved tear strength. The taste of the resulting wafers was good without bitterness and/or throat irritation.

Example 28

Disintegrable oral films containing a taste masked ketoprofen were produced from the following ingredients:

| Component | Quantity (g) |
| --- | --- |
| Ketoprofen | 6.53 |
| Anion exchange resin | 6.42 |
| CMC | 5.57 |
| HV HPMC | 1.76 |
| Lime Flavor | 0.44 |
| Polysorbate 80 | 0.22 |
| Menthol | 0.41 |
| PEG-40 Hydrogenated Castor Oil | 0.80 |
| Sucralose | 0.23 |
| Isomaltidex | 1.00 |
| Lysine Hydrate | 4.22 |
| Purified Water | 73.56 |
| Total | 101.56 |

A vessel was charged with about 73.56 g water and then about 4.22 g lysine hydrate. This composition was mixed until dissolved and then mixed at 500 rpm. Ketoprofen was added slowly, in an amount of about 6.53 g, and mixed for 15 minutes. About 6.42 g DUOLITE® 1093 Cholestyramine anion exchange resin was added slowly under mixing and the resulting composition was mixed for about 30 minutes at 500 rpm. A flavor premixture containing about 0.44 g lime flavor, about 0.22 g Polysorbate 80, and about 0.80 g CREMOPHOR® RH40 PEG-40 Hydrogenated castor oil and 0.41 g menthol and 0.23 g sucralose was formed in a separate beaker and added to the ketoprofen mixture. About 1.00 g isomalt was added and the resulting mixture stirred at 500 rpm for 15 min. About 5.57 g of AQUALON® CMC-7LF sodium CMC and about 1.76 g METOLOSE® 60SH50 HPMC was added and the resulting composition was mixed at 1,900 rpm for 30 minutes. The composition was then sonicated for 10 minutes and de-aerated using an aspirator. The aspirated coating solution was formed into mono-layered wafers using a conventional coating technique. The average weight of the resulting wafers was 63.20 mg (sd=1.33 mg) and thickness was 91 μm (sd=3.0 μm). The formulation produced a film with good mechanical properties, particularly good tear strength. The resulting wafer taste was good without bitterness and/or throat irritation.

HPMC/Pectin Sodium CMC/Pectin and Sodium CMC/HPMC/Pectin Formulations

Example 29

Disintegrable oral films containing a taste masked ketoprofen were produced from the following ingredients:

| Component | Quantity (g) |
| --- | --- |
| Ketoprofen | 6.51 |
| Sodium Hydroxide | 1.02 |
| Anion exchange resin | 6.44 |
| LV HPMC | 4.50 |
| Pectin USP | 2.00 |
| HV HPMC | 2.01 |
| Masking Flavor | 0.30 |
| Lime Flavor | 0.31 |
| Polysorbate 80 | 0.31 |
| Menthol | 0.40 |
| PEG-40 Hydrogenated Castor Oil | 0.40 |
| Sucralose | 0.30 |
| Lysine Hydrate | 2.11 |
| Purified Water | 73.59 |
| Total | 100.20 |

A vessel was charged with about 73.59 g water and then about 1.02 g NaOH. This composition was mixed at 500 rpm. Ketoprofen was added slowly, in an amount of about 6.51 g, and mixed for 15 minutes and sonicated for 5 minutes. While mixing at 500 rpm, about 6.44 g DUO-LITE® 1093 Cholestyramine anion exchange resin was added slowly and the resulting composition was mixed for about 30 minutes at 500 rpm. About 2.11 g lysine hydrate was added to further stabilize the pH. A flavor premixture containing about 0.30 g masking flavor, 0.31 g lime flavor, about 0.31 g Polysorbate 80, and about 0.40 g CREMOPHOR® RH40 PEG-40 Hydrogenated castor oil and 0.40 g menthol and 0.30 g sucralose was added to the ketoprofen mixture and mixed at 500 rpm. About 2.00 g pectin, about 4.50 g PHARMACOAT® 603 HPMC and about 2.01 g METOLOSE® 60SH50 HPMC was added and the resulting composition was mixed at 2,000 rpm for a minimum of 30 minutes. The composition was then sonicated for 10 minutes and de-aerated using an aspirator. The aspirated coating solution was formed into mono-layered wafers using a conventional coating technique. The average weight of the resulting wafer was 56.64 mg (sd=0.68 mg) and thickness was 118 μm (sd=5.8 μm). The resulting wafer taste was good with no bitterness and/or throat initiation and/or burning sensation.

Example 30

Disintegrable oral films containing a taste masked ketoprofen were produced from the following ingredients:

| Component | Quantity (g) |
| --- | --- |
| Ketoprofen | 6.53 |
| Sodium Hydroxide | 1.03 |
| Anion exchange resin | 6.42 |
| CMC | 3.58 |
| Pectin USP | 2.06 |
| HV HPMC | 2.01 |
| Masking Flavor | 0.31 |
| Lime Flavor | 0.33 |
| Polysorbate 80 | 0.30 |
| Menthol | 0.43 |
| PEG-40 Hydrogenated Castor Oil | 0.42 |
| Sucralose | 0.30 |
| Lysine Hydrate | 2.11 |
| Purified Water | 89.50 |
| Total | 115.33 |

A vessel was charged with about 89.50 g water and then about 1.03 g 1N NaOH. This composition was mixed at 500 rpm. Ketoprofen was added slowly until the pH was above 5.5, an amount of about 6.53 g. The ketoprofen containing mixture was stirred for 15 minutes and sonicated for 5 minutes. While mixing at 500 rpm, about 6.42 g DUO-LITE® 1093 Cholestyramine anion exchange resin was added slowly and the resulting composition was mixed for about 30 minutes at 500 rpm. About 2.11 g lysine hydrate was added to further stabilize the pH. A flavor premixture containing about 0.31 g masking flavor, 0.33 g lime flavor, about 0.30 g Polysorbate 80, and about 0.42 g CREMOPHOR® RH40 PEG-40 Hydrogenated castor oil and 0.43 g menthol and 0.30 g sucralose was added to the ketoprofen mixture and mixed at 500 rpm. About 2.06 g pectin, about 3.58 g AQUALON® CMC-7LF sodium CMC cellulose gum and about 2.01 g METOLOSE® 60SH50 HV HPMC was added and the resulting composition was mixed at 2,000 rpm for 30 minutes. The composition was then sonicated for 10 minutes and do-aerated using an aspirator. The aspirated coating solution was formed into mono-layered wafers using a conventional coating technique. The average weight of resulting wafers was 53.08 mg (sd=0.97 mg) and thickness was 79 μm (sd=3.4 μm). The film had good mechanical properties. The taste of the resulting waters was good without bitterness and/or throat irritation.

Example 31

Disintegrable oral films containing a taste masked ketoprofen were produced from the following ingredients:

| Component | Quantity (g) |
| --- | --- |
| Ketoprofen | 4.51 |
| Sodium Hydroxide | 0.71 |
| Anion exchange resin | 4.43 |
| CMC | 2.47 |
| Pectin USP | 1.42 |
| HV HPMC | 1.39 |
| Masking Flavor | 0.21 |
| Lime Flavor | 0.23 |
| Polysorbate 80 | 0.21 |
| Menthol | 0.30 |
| PEG-40 Hydrogenated Castor Oil | 0.29 |
| Sucralose | 0.21 |
| Lysine Hydrate | 1.45 |
| Purified Water | 81.91 |
| Total | 99.73 |

About 20 grams of water was added to about 80 grams of the remaining material from Example 27 to reduce viscosity. The resulting coating solution was then formed into monolayered wafers using a conventional coating technique. The average weight of the resulting wafers was 40.86 mg (sd=0.37 mg) and thickness was 65 μm (sd=2.2 μm). The resulting wafers tasted good without bitterness and/or throat irritation.

Example 32

Disintegrable oral films containing a taste masked ketoprofen were produced from the following ingredients:

| Component | Quantity (g) |
| --- | --- |
| Ketoprofen | 4.52 |
| Sodium Hydroxide | 0.71 |
| Anion exchange resin | 4.44 |
| CMC or HV HPMC | 3.04 |
| Pectin USP | 3.03 |
| Masking Flavor | 0.20 |
| Lime Flavor | 0.33 |
| Polysorbate 80 | 0.20 |
| Menthol | 0.40 |
| PEG-40 Hydrogenated Castor Oil | 0.81 |
| Sucralose | 0.30 |
| Lysine Hydrate | 1.48 |
| Purified Water | 80.76 |
| Total | 100.23 |

A vessel was charged with about 80.76 g water and then about 0.31 g 1N NaOH. This composition was mixed at 500 rpm. Ketoprofen was added slowly until the pH was above 5.5, an amount of about 4.52 g. The ketoprofen containing mixture was sonicated for 5 minutes and 0.4 g of 1N NaOH was added, and the resulting composition mixed at 500 rpm until the pH was 6.5 to 6.8. While mixing at 500 rpm, about 4.44 g DUOLITE® 1093 Cholestyramine anion exchange resin was added slowly and the resulting composition was mixed for about 30 minutes at 500 rpm. About 1.48 g lysine hydrate was added to further stabilize the pH. A flavor premixture containing about 0.20 g masking flavor, 0.33 g lime flavor, about 0.20 g Polysorbate 80, and about 0.81 g CREMOPHOR® RH40 PEG-40 Hydrogenated castor oil and 0.40 g menthol and 0.30 g sucralose was added to the ketoprofen mixture and mixed at 500 rpm. About 3.03 g pectin and about 3.04 g AQUALON® CMC-7LF sodium CMC or METOLOSE® 60SH50 HPMC was added and the resulting composition was mixed at 2,000 rpm for 30 minutes. The composition was then sonicated for 10 minutes and do-aerated using an aspirator. The aspirated coating solution was formed into mono-layered wafers using a conventional coating technique. The average weight of a few wafers was 43.87 mg (sd=2.03 mg) and thickness was 64 µm (sd=3.4 µm). The taste of the resulting wafers was good without bitterness and/or throat irritation.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains. Therefore, the present invention should not be limited to any single illustrative embodiment described herein.

By way of summary, the present invention thus generally concerns:

(1). An edible oral film strip comprising
at least one water dispersible or water disintegrable film forming polymer,
a basic active pharmaceutical ingredient and
at least one cationic exchange resin as a primary taste masking agent.

(2). An edible oral film strip as described in (1) above, wherein said strip further comprises an edible acidic agent.

(3). An edible oral film strip as described in one or more of (1) through (2) above, wherein said strip further comprises one or more secondary taste masking agents.

(4). An edible oral film strip as described in one or more oft 1) through (3) above, wherein the secondary taste masking agents are selected from one or more of sweetener(s), flavoring agent(s), cooling sensation agent(s), and taste receptor blocker(s).

(5). An edible oral film strip as described in one or more of (1) through (4) above, wherein said secondary taste masking agent comprises at least one sweetener selected from dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin, dextrates.

(6). An edible oral film strip as described in one or more of (1) through (5) above, wherein said secondary taste masking agent includes a sweetener composition comprising isomalt and a sweetener selected from one or more of sucralose aspartame, saccharine and acesulfame.

(7). An edible oral film strip as described one or more of (1) through (6) above, wherein said secondary taste masking agent includes at least one flavoring agent selected from essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, tutti fruitti, apple, coffee, plum, watermelon, nuts, green tea, grapefruit, banana, butter, and chamomile.

(8). An edible oral film strip as described in one or more of (1) through (7) above, wherein the secondary taste masking agent comprises a cooling sensation agent selected from one or more of essential oils or extracts of menthol, wintergreen, peppermint, sweet mint, spearmint.

(9). An edible oral film strip as described in one or more of (1) through (8) above, wherein the secondary taste masking agent comprises PEG-40 Hydrogenated Castor Oil as a taste receptor blocker.

(10). An edible oral film strip as described in one or more of (1) through (9) above, wherein the active ingredient is present in the oral film strips in an amount ranging from about 3 mg to about 75 mg per unit.

(11). An edible oral film strip as described in one or more of (1) through (10) above, wherein the film forming polymer is one of more of cellulose, cellulose derivatives, synthetic or natural gums, methacrylic acid polymers, methacrylic acid copolymers, acrylic acid polymers, acrylic acid copolymers, polyacrylamides, polyalkylene oxides, polyalkylene glycols, carrageenan, pullunan, locust bean gums, bean starches, polyvinyl pyrrolidone, polyvinyl alcohol, alginic acid, salts of alginic acid, carboxyvinyl polymers, pectin, pectin derivatives, xanthan gum, xanthan gum derivatives, pea starch and starch derivatives and mixtures thereof.

(12). An edible oral film strip as described in one or more of (1) through (11) above, wherein the film forming polymer is a cellulose derivative selected from methyl cellulose, ethyl cellulose, hydroxyethyl cellulose, hydroxypropyl methyl cellulose, carboxymethyl cellulose, sodium carboxymethyl cellulose, and mixtures thereof.

(13). An edible oral film strip as described in one or more of (1) through (12) above, wherein the film forming polymer is a mixture of sodium carboxymethylcellulose or methylcellulose and hydroxypropylmethylcellulose.

(14). An edible oral film strip as described in one or more of (1) through (13) above, wherein the oral film strip comprises at least one emulsifier selected from castor oil derivatives, cetyl and palmityl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, polyethylene sorbitan fatty acid esters and mixtures thereof.

(15). An edible oral film strip as described in one or more of (1) through (14) above, wherein the oral film strip further comprises at least one ancillary component selected from bioadhesives for mucosal binding, buffering agents for additional pH control, coloring agents, stabilizing agents, antioxidants, fillers, permeation enhancers, plasticizers and microbial preservatives.

(16). An edible oral film strip as described in one or more of (1) through (15) above, wherein said oral film strip comprises basic active pharmaceutical ingredient, cationic exchange resin, an acidic agent, and secondary taste masking agents comprising a taste receptor blocking agent, a cooling sensation agent, at least two sweeteners and one or more flavoring agents.

(17). An edible oral film strip as described in one or more of (1) through (16) above, wherein said oral film strip comprises basic active pharmaceutical ingredient in an amount ranging from about 10 to 50 wt % based on the weight of the dry oral film strip.

(18). An edible oral film strip as described in one or more of (1) through (17) above, wherein said oral film strip comprises at least one cationic exchange resin in an amount ranging from about 12 to 50 wt % based on the weight of the dry oral film strip.

(19). An edible oral film strip as described in one or more of (1) through (18) above, wherein said oral film strip comprises a taste receptor blocking agent in an amount ranging from about 0.17 to 6.5 wt % based on the weight of the dry oral film strip.

(20). An edible oral film strip as described in one or more of (1) through (19) above, wherein said oral film strip comprises a cooling sensation agent in an amount ranging from about 0.7 to 3.0 wt % based on the weight of the dry oral film strip.

(21). An edible oral film strip as described in one or more of (1) through (20) above, wherein said oral film strip comprises a sweetener composition comprising at least two sweeteners in amount ranging from about 0.25 to 3.0 wt % based on the weight of the dry oral film strip.

(22). An edible oral film strip as described in one or more of (1) through (21) above, wherein said oral film strip comprises one or more flavouring agents in an amount ranging from about 0.3 to 4.5 wt % based on the weight of the dry oral film strip.

(23). A method of preparing an edible oral film strip as described in one or more of (1) through (22) above, comprising dissolving or suspending a clinically effective amount of a basic active pharmaceutical ingredient into a pharmacologically approved solvent to form an active-ingredient solution;

optionally adjusting the pH of the active-ingredient solution to a more acidic pH;

introducing at least one cationic ion exchange resin into the optionally pH adjusted active ingredient solution;

admixing the active-ingredient/anion exchange resin solution with one or more water-soluble or water-miscible polymers to produce a film-forming composition;

optionally incorporating one or more excipients selected from cooling agents, emulsifiers, flavouring agents, sweeteners, taste receptor blockers or ancillary excipients, optionally sonicating and/or vacuuming the film-forming composition to remove entrapped air, coating, extruding or casting the optionally deaerated film forming composition onto a casting substrate to form a wet film.

drying the coated, extruded or cast wet film;

removing the dried film from the casting substrate; and cutting the dried film into individual oral film strips.

(24). A method of administering an edible oral film strip comprising applying an edible oral film strip dosage as described in one or more of (1) through (23) above to the oral cavity of a patient, optionally via a mucoadhesive, and allowing the dosage to dissolve for subsequent absorption in the GI tract of the patient.

As used herein and in the appended claims, the term "a" as an article may connote either the singular or the plural.

The invention claimed is:

1. An edible oral film strip comprising
at least one water dispersible or water disintegrable film forming polymer,
an active pharmaceutical ingredient with a positive charge, and
at least one cationic exchange resin as a primary taste masking agent,
wherein said strip further comprises an edible acidic agent,
and said strip ha a maximum thickness ranging from 50 to 120 µm.

2. An edible oral film strip as claimed in claim 1, wherein said strip further comprises one or more secondary taste masking agents.

3. An edible oral film strip as claimed in claim 2, wherein the secondary taste masking agents are selected from one or more of sweetener(s), flavoring agent(s), cooling sensation agent(s), and taste receptor blocker(s).

4. An edible oral film strip as claimed in claim 3, wherein said secondary taste masking agent comprises at least one sweetener selected from dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin, dextrates.

5. An edible oral film strip as claimed in claim 3, wherein said secondary taste masking agent includes a sweetener composition comprising isomalt and a sweetener selected from one or more of sucralose, aspartame, saccharine and acesulfame.

6. An edible oral film strip as claimed in claim 2, wherein said secondary taste masking agent includes at least one flavouring agent selected from essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, tutti fruitti, apple, coffee, plum, watermelon, nuts, green tea, grapefruit, banana, butter, and chamomile.

7. An edible oral film strip as claimed in claim 2, wherein the secondary taste masking agent comprises a cooling sensation agent selected from one or more of essential oils or extracts of menthol, wintergreen, peppermint, sweet mint, spearmint.

8. An edible oral film strip as claimed in claim 2, wherein the secondary taste masking agent comprises PEG-40 Hydrogenated Castor Oil as a taste receptor blocker.

9. An edible oral film strip as claimed in claim 1, wherein the active ingredient is present in the oral film strips in an amount ranging from about 40.86 mg to about 75 mg per unit.

10. An edible oral film strip as claimed in claim 1, wherein the film forming polymer is one of more of cellulose, cellulose derivatives, synthetic or natural gums, methacrylic acid polymers, methacrylic acid copolymers, acrylic acid polymers, acrylic acid copolymers, polyacrylamides, polyalkylene oxides, polyalkylene glycols, carrageanan, pullunan, locust bean gums, bean starches, polyvinyl pyrrolidone, polyvinyl alcohol, alginic acid, salts of alginic acid, carboxyvinyl polymers, pectin, pectin derivatives, xanthan gum, xanthan gum derivatives, pea starch and starch derivatives and mixtures thereof.

11. An edible oral film strip as claimed in claim 1, wherein the film forming polymer is a cellulose derivative selected from methyl cellulose, ethyl cellulose, hydroxyethyl cellulose, hydroxypropyl methyl cellulose, carboxymethyl cellulose, sodium carboxymethyl cellulose, and mixtures thereof.

12. An edible oral film strip as claimed in claim 1, wherein the film forming polymer is a mixture of sodium carboxymethylcellulose or methylcellulose and hydroxypropylmethylcellulose.

13. An edible oral film strip as claimed in claim 1, wherein the oral film strip comprises at least one emulsifier selected from castor oil derivatives, cetyl and palmityl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, polyethylene sorbitan fatty acid esters and mixtures thereof.

14. An edible oral film strip as claimed in claim 1, wherein the oral film strip further comprises at least one ancillary component selected from bioadhesives for mucosal binding, buffering agents for additional pH control, coloring agents, stabilizing agents, antioxidants, fillers, permeation enhancers, plasticizers and microbial preservatives.

15. An edible oral strip as claimed in claim 1, wherein said oral film strip comprises
said active pharmaceutical ingredient in an amount ranging from about 25.3 to 50 wt % based on the weight of the dry oral film strip;
at least one cationic exchange resin in an amount ranging from about 12 to 50 wt % based on the weight of the dry oral film strip;
an effective amount of an acidic agent,
a taste receptor blocking agent in an amount ranging from about 0.17 to 6.5 wt % based on the weight of the dry oral film strip;
a cooling sensation agent in an amount ranging from about 0.7 to 3.0 wt % based on the weight of the dry oral film strip;
a sweetener composition comprising at least two sweeteners in amount ranging from about 0.25 to 3.0 wt % based on the weight of the dry oral film strip; and
one or more flavouring agents in an amount ranging from about 0.3 to 4.5 wt % based on the weight of the dry oral film strip.

16. A method of preparing an edible oral film strip as claimed in claim 1, comprising
dissolving or suspending a clinically effective amount of said active pharmaceutical ingredient into a pharmalogically approved solvent to form an active-ingredient solution;
optionally adjusting the pH of the active-ingredient solution to become more acidic;
introducing at least one cationic ion exchange resin into the optionally pH adjusted active ingredient solution;
admixing the active-ingredient/cationic ion exchange resin solution with one or more water-soluble or water-miscible polymers to produce a film-forming composition;
optionally incorporating one or more excipients selected from cooling agents, emulsifiers, flavouring agents, sweeteners, taste receptor blockers or ancillary excipients,
optionally sonicating and/or vacuuming the film-forming composition to remove entrapped air;
coating, extruding or casting the optionally deaereated film forming composition onto a casting substrate to form a wet film,
drying the coated, extruded or cast wet film;
removing the dried film from the casting substrate; and
cutting the dried film into individual oral film strips.

17. A method of administering an edible oral film strip as claimed in claim 1, said method comprising applying an edible oral film strip dosage to the oral cavity of a patient, optionally via a mucoadhesive, and allowing the dosage to dissolve for subsequent absorption in the GI tract of the patient.

18. An edible oral film strip as claimed in claim 1, wherein the active pharmaceutical ingredient is in an amount ranging from 25.3 to 50 wt % based on the weight of the dry oral film strip, and the strip does not include simethicone.

19. An edible oral film strip as claimed in claim 1, wherein said strip has a thickness ranging from 64 to 115 μm, and has a dissolution time of less than 15 minutes.

20. An edible oral film strip as claimed in claim 1, wherein one of the water dispersible or water disintegrable film forming polymers is hydroxypropylmethylcellulose having a viscosity ranging from 40 to 100 mPas.

21. An edible oral film strip comprising
an active pharmaceutical ingredient with a positive charge,
at least one cationic exchange resin as a primary taste masking agent,
a mixture of cellulose derivatives comprising
(i) a lower viscosity cellulose having a viscosity ranging from about 1.5 to 2.5 mPas and
(ii) a higher viscosity cellulose having a viscosity ranging from greater than 25 mPas to 100 mPas
wherein said mixture of cellulose derivatives is present in a weight ratio ranging from about 1.5:1 to 6:1, based upon lower viscosity cellulose derivative:higher viscosity cellulose derivative.

22. An edible oral film strip as claimed in claim 21, wherein said strip has a maximum thickness ranging from 50 to 120 μm.

* * * * *